United States Patent
Contreras et al.

(10) Patent No.: US 7,125,970 B1
(45) Date of Patent: Oct. 24, 2006

(54) **DRUG TARGETS IN *CANDIDA ALBICANS***

(75) Inventors: Roland Henri Contreras, Ghent (BE); Bart Jozef Maria Nelissen, Beerse (BE); Marianne Denise De Backer, Beerse (BE); Walter Herman Maria Louis Luyten, Beerse (BE); Jasmine Elza Viaene, Ghent (BE); Marc George Logghe, Ghent (BE); Jorge Eduardo Vialard, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/857,372

(22) PCT Filed: Dec. 6, 1999

(86) PCT No.: PCT/EP99/09833

§ 371 (c)(1),
(2), (4) Date: Jun. 4, 2001

(87) PCT Pub. No.: WO00/34481

PCT Pub. Date: Jun. 15, 2000

(30) Foreign Application Priority Data

Dec. 4, 1998 (EP) .................................. 98204122

(51) Int. Cl.
*C07H 21/02* (2006.01)
*C07H 21/04* (2006.01)
*C12N 1/20* (2006.01)
*C12N 15/00* (2006.01)

(52) U.S. Cl. ................. 536/23.1; 536/23.7; 435/252.3; 435/320.1

(58) Field of Classification Search ............... 536/23.1, 536/23.7; 435/252.3, 320.1; 514/44
See application file for complete search history.

(56) References Cited

U.S. PATENT DOCUMENTS

| 5,576,428 | A | * | 11/1996 | Butler et al. ............... 536/24.1 |
| 2005/0042646 | A1 | * | 2/2005 | Davidson et al. .............. 435/6 |
| 2005/0147694 | A1 | * | 7/2005 | Brewer ....................... 424/646 |

OTHER PUBLICATIONS

Daly et al. Gene, vol. 187, No. 2, pp. 151-158, 1997.*
NIH, Gene Therapy Report, Dec. 1995.*

* cited by examiner

*Primary Examiner*—Mark Navarro

(57) ABSTRACT

The present invention is concerned with the identification of genes or functional fragments thereof from *Candida albicans* which are critical for growth and cell division and which genes may be used as selective drug targets to treat *Candida albicans* associated infections. Novel nucleic acid sequences from *Candida albicans* are also provided and which encode the polypeptides which are critical for growth of *Candida albicans*. Methods for the identification of anti-fungal compounds which inhibit fungal or yeast growth are also contemplated.

5 Claims, 4 Drawing Sheets

SEQUENCE LISTING

```
<160> NUMBER OF SEQ ID NOS: 24

<210> SEQ ID NO 1
<211> LENGTH: 438
<212> TYPE: DNA
<213> ORGANISM: Candida albicans

<400> SEQUENCE: 1
aacagctggt cttctgctaa tacattcaac cctttccata tctatactcc aacaatatga      60
taactgatga acaattgaat accattgcat tgacatttgg ttttgcttca ataatattaa     120
tcataatata tcatgccata tctactaatg tacataaatt agaagatgaa accccatcat     180
cttcatttac cagaacaaat actactgaaa ctactgttgc aagtaagaaa aagaagtaat     240
aactgatgga tttttcttcc taccaccaat tgaataatgc tagacttgtt ggtgtgctac     300
aaatatttca aaagaaaata cgaatacttt ataaaatggt aagaacggaa gatggtttct     360
catttataca ctaaatacaa atcacataca catacacaaa cacaaataca tacatacacc     420
tatatccctt tatttgat                                                   438

<210> SEQ ID NO 2
<211> LENGTH: 1380
<212> TYPE: DNA
```

<213> ORGANISM: Candida albicans

<400> SEQUENCE: 2

| | | | | | |
|---|---|---|---|---|---|
| atgttaaaaa | cactaactca | aactttacgc | ttaactggga | aagctttccc | aaaggtccgt | 60 |
| ccggccttga | tcagaaccta | cgctgccttc | gaccgttcta | aacctcatgt | caacattggt | 120 |
| actattggtc | atgttgatca | tggtaaaact | acattgactg | ctgctatcac | caaagtttta | 180 |
| gccgaacaag | gtggtgccaa | cttcttggat | tatggttcta | ttgatagagc | tccagaagaa | 240 |
| agagctagag | gtatcactat | ttccactgcc | cacgttgaat | acgaaaccaa | gaacagacac | 300 |
| tatgcccacg | ttgattgtcc | aggacacgct | gattatatca | aaatatgat | tactggtgcc | 360 |
| gctcaaatgg | atggtgctat | cattgttgtt | gctgccactg | atggtcaaat | gcctcaaacc | 420 |
| agagaacatt | tgttattggc | cagacaagtt | ggtgttcaag | acttggttgt | gtttgtcaac | 480 |
| aaagtcgata | ctattgatga | ccctgaaatg | ttggaattag | tcgaaatgga | aatgagagaa | 540 |
| ttgttatcca | cctacggttt | tgatggtgac | aacactccag | ttattatggg | atctgcttta | 600 |
| atggctttgg | aagacaagaa | accagaaatt | ggtaaggaag | ctatcttgaa | attgttagat | 660 |
| gctgtcgatg | aacacattcc | aactccatca | agagacttgg | aacaaccatt | tttgttacca | 720 |
| gttgaagacg | tgttctccat | ctccggtaga | ggaactgttg | tcactggtag | agttgaaaga | 780 |
| ggtgttttga | gaaggggtga | agaaatcgaa | attgttggtg | gttttgacaa | accttacaag | 840 |
| actactgtta | ccggtattga | aatgttcaaa | aaagaattag | actctgctat | ggctggtgac | 900 |
| aactgtggtg | ttttgttaag | aggtgttaaa | agagatgaaa | tcaagagagg | tatggttttg | 960 |
| gccaaaccag | gtactgctac | ttctcacaag | aagttcttgg | cttccttgta | tattttgact | 1020 |
| tccgaagaag | tggtcgttc | cactccattt | ggtgaaggtt | acaagcctca | atgcttcttc | 1080 |
| agaactaacg | atgtcactac | cacattttca | ttcccagaag | gagaaggtgt | tgatcattct | 1140 |
| caaatgatca | tgccaggtga | caacattgaa | atggttggtg | aattgatcaa | atcttgtcca | 1200 |
| ttagaagtca | accaacgttt | caacttgaga | gaaggtggta | aaactgttgg | tactggtttg | 1260 |
| attaccagaa | tcatcgaata | aacagaatgt | gcactgtgaa | taataaaaag | aaaagaggta | 1320 |
| tatataggtg | actttgtatt | ttgtattgaa | caataaaatt | ctgtaaatag | taagggcctc | 1380 |

<210> SEQ ID NO 3
<211> LENGTH: 2283
<212> TYPE: DNA
<213> ORGANISM: Candida albicans

<400> SEQUENCE: 3

| | | | | | |
|---|---|---|---|---|---|
| gaattcgccc | ttaagcactc | gtttcaacta | tacattcagt | aacaacaccc | ttaatttacc | 60 |
| aaactacatt | aatggaagta | acacaacgga | cgcagagtca | gacacaacca | acacaacagt | 120 |
| caccgacaac | tcagacgcaa | acccaaagca | aagaggacca | gaataggatt | tgtcaattga | 180 |
| tttgctccac | gggtcagttt | ggcaattatg | atttgaatat | caacgataaa | actatcgtac | 240 |
| aaggtaaaat | gacgtggtat | tttggaagag | accccaactc | agatttgcaa | gtggcgtcgt | 300 |
| cgtcgagaat | tcaaacaag | cattttcaaa | tctggctcaa | cttcaatgat | aaatcactat | 360 |
| ggataaagga | cacttcaact | aacgggacac | accttaacaa | cagtcgattg | gtgaaaggat | 420 |
| caaactacct | tcttaatcag | ggtgatgaaa | tagcagtagg | ggttggtaga | gacgaggacg | 480 |
| ttgtgaggtt | tgtcgttgtc | tttggtgaca | atacaacccc | ggcaaagcta | cctgattcga | 540 |
| ccaacacaat | taaagatgaa | ggaatataca | aagactttat | tgtgaaaaat | gaacgatag | 600 |
| gccaaggagc | atttgccact | gtgaaaaagg | cgattgaacg | atctacgggc | gagtcgtacg | 660 |

```
cggtgaagat tataaatcga agaaaagcat taaataccgg tggtggaagt gccatggcag      720
gagtggaccg tgaattgtcc atattagagc ggctcaacca cccaaatata gttgctctaa      780
aagcttttta tgaagatatg gacaattact atattgtgat ggaattggtg ccgggcggtg      840
atttgatgga ctttgtggct gcaaacggtg caataggaga agacgcaaca caagtgatca      900
cgaaacagat tctagaagga attgcctatg ttcataattt aggaatctcc catcgtgatt      960
tgaagccaga taatattttg attatgcaag atgacccaat acttgttaaa atcaccgact     1020
ttggattggc aaaattcagt gacaatctga cgtttatgaa acttttttgt ggtacattgg     1080
cgtatgttgc tcccgaagtt atcaccggta agtatggatc atcgcagatg gaactgcaac     1140
aaaaggacaa ctactcttcc ttggttgaca tttggtcttt gggatgtttg gtttatgtac     1200
ttttaacttc tcatttacca ttcaacggga aaaccagca acaaatgttt gccaagatca     1260
aaaggggcga atttcatgag gctccattaa attcatacga catttctgaa gacggaagag     1320
atttcttgca gtgctgccta caggttaatc ctaaactaag gatgacggct gctgaagctt     1380
tgaaacataa atggttgcaa gacttgtatg aagaggattc tgtcaaatca ttgagtttat     1440
cgcaatcaca gtcgcaacaa tctcgaaaga tagataatgg tatccatatc gaatcattga     1500
gcaaaattga tgaagacgtt atgcttcgtc cattggatag cgaaagaaat aggaaatcaa     1560
gtaaacagca agatttcaag gtacccaagc gtgtgattcc gttatctcaa catcctgcaa     1620
caccgttacc aatgtcacaa ccgaaaaaga ggccgtatca aatagaccct agaacaaaca     1680
aaaaagtcga tttggaagaa cctctgacaa gcaagaaagt caagctaagt gattccgttg     1740
ttgcggaaga ctacttgaag ttggggccac ttgcaaattc gttattccaa gaaacaataa     1800
atatttcaaa gtccccgttt tctttcggaa gaatgcgact tgtgattgc gagatagacg      1860 acgacagact atccaaactt cattgtgtca ttaccaaaga aaacgactct atatggttat     1920
tggataagag tactaactcg tgcttggtca acaatactag tgttggaaaa ggcaacaaag     1980
ttttgcttag aggaggggag atattacatc tcttctttga cccattgtca ctgcaacata     2040
taggtttcaa agtagtcctt gttgatcaac tgtctggtga acataagagt caagtggagg     2100
ttttgaaaca aacctcagaa gaaatgaata ttattccact tatttctggt ttaagtagta     2160
taagttcata gatttagcat atatacaagc atttcctata gaaacaaagg ttcattaatt     2220
tagttattta cctccatgca attacattta cttcttcttc caagggcgaa ttctgcagat     2280
atc                                                                   2283

<210> SEQ ID NO 4
<211> LENGTH: 826
<212> TYPE: DNA
<213> ORGANISM: Candida albicans

<400> SEQUENCE: 4
atgggtagta tgtgaagata caatattgaa agtgtttact agaatatcta agatgtttga       60
gcccatggac attttggat ttgataatta aaaaagtag caatagatta ttgcgttgga       120
gaaagaatca ccatagttgc aagatttgat agatgttaaa atgttcacgc aggcgaaaga      180
tgtaacatct cttaaagtaa gagaatatg gacatgaata aaaatagata gcactatttt      240
ggaacttgtt gaagatatta aaatagaatg ggatttcaac atagatattc aaagtaacga      300
aacctcacaa tcaaataaaa acaacagtaa tactaacaat tcaatttta ttttatatga      360 gggtactcca tctttaggta aacgtcacaa caaatctcac accttatgta acagatgtgg     420
```

-continued

| | |
|---|---|
| ccgtcgttca ttccacgtcc aaaagaagac ctgttcttct tgtggttacc cagctgctaa | 480 |
| aatgagatct cacaactggg ccttaaaagc caaaagaaga agaactactg gtaccggtag | 540 |
| aatggcttac ttgaaacacg ttaccagaag attcaagaac ggtttccaaa ctggtgttgc | 600 |
| taaagctcaa accccttccg cttaaactaa ttactgaagt tattggtcat gcattagtca | 660 |
| ttattcatta aagtcatgtt aagcatagca aaggaagaat tggttagatt cttgtttaaa | 720 |
| atgtaatgac tatttaatat ctgtttaaat aagaggttta gtctttattt ttttacgtat | 780 |
| acaccaaaaa aaaagaaac aaataaaatc tgtatattaa tgttgg | 826 |

<210> SEQ ID NO 5
<211> LENGTH: 978
<212> TYPE: DNA
<213> ORGANISM: Candida albicans

<400> SEQUENCE: 5

| | |
|---|---|
| atgggtacta gtacaagtga agcattgaag aacatcaaaa acaaacagcg aagacagaaa | 60 |
| gttttttgcag aaataaaaca tgaaaagaat aaacaacgtc ataagcaaag agccgaaaga | 120 |
| gctaaggaag aaagagaaaa ccccgaatta agagaggaaa gaatagcagc taatatccca | 180 |
| gatactatag atagcaaacg tatttatgat gagactatag ctgctgaagt tgaaggagat | 240 |
| gacgagtttc agtcatattt cactaacttg ttggaagaac caaagatttt gttgacaaca | 300 |
| agtgccaatg ctaaaaaacc ggcctatgaa tttgcagaca tgatcatgga cttttaccg | 360 |
| aatgtgacat ttatcaaaag gaagaaggaa tatacaatgc aagatatggc caaatattgc | 420 |
| tcgaatagag acttcactgc attgcttgtc atcaacgaag acaagaagaa ggtcaatggt | 480 |
| ataacgctca tcaatttacc tgaagggcca acatttttatt tttcgattac atcaatagtt | 540 |
| gatgggaaaa gaattaaggg acacgggaaa gctggtgatt atttacctga gattgtattg | 600 |
| aataatttca attcaagatt gggtaaaact gtgggaagac tattcaaag tattttccct | 660 |
| cataaacctg aacttcaagg aagacaagtg attactttgc acaatcaacg tgattatatt | 720 |
| tttttcagaa gacatagata tattttcaga aatgaggaaa aggttggatt gcaggaattg | 780 |
| ggtccgcagt ttacattaaa gctaagaaga atgcaaaagg gagtacgtgg tgatgttgtt | 840 |
| tgggaacaca gaccagatat ggaaagagat aagaagaagt tttatttata agcgggtgta | 900 |
| taaaggtagt agtagtgcgt ttataagtat gtgtgtgtgt ttatgcatag atgtgtaaag | 960 |
| agtaatacag ctaattcg | 978 |

<210> SEQ ID NO 6
<211> LENGTH: 619
<212> TYPE: DNA
<213> ORGANISM: Candida albicans
<220> FEATURE:
<221> NAME/KEY: modified_base
<222> LOCATION: (597)..(598)
<223> OTHER INFORMATION: a, c, t or g
<220> FEATURE:
<221> NAME/KEY: modified_base
<222> LOCATION: (613)
<223> OTHER INFORMATION: a, c, t or g

<400> SEQUENCE: 6

| | |
|---|---|
| aactaatttg tttaaacatc aataccaaga agttttaca attcaatccc acatacacca | 60 |
| ttaattatga attctgaaaa gattattgaa gttatcattg ctattttctt accaccagta | 120 |
| gctgtgttta tgaaatgtgg tgccactacc ccattatgga ttaacttggt attatgtatc | 180 |
| tttatttggt tccctgctat cttacatgcc ttatacgttg tgttgaaaga ttaaacaaac | 240 |

-continued

```
accagagatt tactgcttga tgaattgatt actccaaaga gttgtgacta gttcccagtg      300 tgttttttt  gccttccaac tttcttttac attttccat  tactaccact gtcttccccc     360
ctattttgca gagttttcaa aatttatcca aaacatgtta gtcattaaac catattatta     420
taattattct ttttgtatt  ttttccctt  aaaacacgtt aatttattaa tcgtttcgtt     480
gtttggtatt ttatttttt  gtatttatca attggaatat atatctatac atgaatttat     540
tatccattgt accaattgtt aaaacatttt gttagttttt tgttactagt ataaaannat     600
aataaaagtt tanttcaac                                                  619

<210> SEQ ID NO 7
<211> LENGTH: 2319
<212> TYPE: DNA
<213> ORGANISM: Candida albicans

<400> SEQUENCE: 7
atgacattag ggttcgataa attcataagc aaggtcagca ctcatagacg tcaatctgaa      60
ccatcaatct tggaaatcgc agccaccaat tctcaaaata aatcgagaag gctaagtatg     120
gataatggtc attgttatgt tcgtgaatca actaataatc atcatcattt aaataccgtc     180
gttgataatt tacgacagcg tgcgggatcg ttttcattta tttcacatca ccataatcac     240
catcagaata gtcacgataa ttatactgtc gatcccctta catcaaacgg agcacgaatt     300
tcccgatcac gttcacgttc caaatcagtt gggcacggag aagcaatatc accagcgtat     360
ttttccaaga ataaaaccaa agatttagtg aaacaggaaa cagcacatat cattctgaag     420
aaattactca acatgttaca agatttggat ttacaaaacc ctattgcatt gaaaacaata     480
tcacaaggtt cagaatcaaa gttttgtaaa atctacgtgt ctaacactaa taattgtatt     540
tacttaccag cagcaagttc aacaagtttc acttatgaag atgatgaaaa tggcggcgtt     600
ataattgctg aagatagaaa tgatgaaatg ccaacagcag ttaataacaa tactttgtca     660
atggatagta taaatcattc agagactgat ttcctggatt ctccaccacc tccagattta     720
ttttctaaaa tgaaatcatt ccattcacca aattacttga cttcaaaaat cgattctgaa     780
tgtccaattc cacatacatt tgctgtgatt gttgaattaa ccaaggactc tttgattatt     840
aaagatcttc atttccaatt tcagtcatta actaccattt tatggccaac tggggatgca     900
tataatcgga ctcatgccaa ggagaaattt accattggga atatggaatg cgtacatct      960 ttaagcgacg ccgactatta tatcaatagt tctaattcca acgatgttaa gctgaaaaac    1020
ttgggtcctg aagatcttat taatcgaact agagaataca aattaatcga tattgaagaa    1080
ccaaacaatt catcaaacag tttactggat gatgacatgg atattaataa tattacgtcg    1140
ccattatcaa cgtcaccaac atcaagttca acttcaacaa attcaacctc caactcattg    1200
ggttcagatt catataaagc tggtctttat gtattttat  taccaatctt attgccagaa    1260
catattcctg cttccattgt ttctattaat ggttcattgg ctcatacatt actggttgaa    1320
tgcaataaat atactgataa gttgaatcgg aaatcaaaag tatcagcatc gtacaattta    1380
cctatggtcc gtactccacc aaacattggt aattccattg ctgataagcc aatttatgtt    1440
aataggattt ggaatgatgc cgtacattat attataactt tcccccgcaa atatgttact    1500
ttgggttgtg aacacatgat aaatgtgaaa ttactgccca tggtgaaaga tgtggttatc    1560
aagcgtatta aatttaatgt attggagaga ataacttatg tttccaaaaa tttatcacga    1620
gaatatgatt atgatagtga agacccctat tgtattcatc cagtttctaa agaaaataaa    1680
```

-continued

```
gtacgtgaac gtgttgtgtc gttatatgaa ttgaaaacga aggcaaaaca atcttctggt    1740
ggacatcttg aagcttataa acaagaagtt atgaaatgtc cggaaaataa ccttttattt    1800
tcttgttatg aggttgaaaa tgataataat aacggcaacg gcaacggcaa cggcaacgga    1860
aacaagaacg ttaaacaaaa gaataaagat caaccaatga ttgctacacc tttagatatc    1920
aatgtttctt taccattttt aactactatg tctgatagtt taattatgac atcagccata    1980
gaagaagaag gttcagatct gcctcataca tcaagaagag ggtcggcagt gagtatgact    2040
gataataata ctaccccaag taacaataac cctttatctc catttttggg agcagtggaa    2100
actaatggtc ctagtataaa tgaaattggt gatcatacat tattccctga ttctaatttt    2160
cgacatattg aaattaaaca tcgattacaa gttacattta ggatttctaa accggatctg    2220
gataataaaa tgcatcatta tgaagtggtt attgatatccc ccatcgtttt acttagttca    2280
aaatgtcaag aagattctcc tcctccttat agttctgta                           2319
```

<210> SEQ ID NO 8
<211> LENGTH: 255
<212> TYPE: DNA
<213> ORGANISM: Candida albicans

<400> SEQUENCE: 8

```
aacgttcgtg caaaaggcta tactggtgat atccacgcag atgaagagca agtttaatca     60
actctttgtc aattaatgct gtacttgttt tcattttatt tgctggcatt taaagaatac    120
ccatagttca gaaaataaaa ttgaaaaatt taaaaaaaaa cgcaatatca ttcattttttt   180 ttgttttttt gacaataata ttaatatgta gttaccaatg ttttagatt ttatatgttt     240 tgaaaaaata gtttg                                                    255
```

<210> SEQ ID NO 9
<211> LENGTH: 119
<212> TYPE: DNA
<213> ORGANISM: Candida albicans
<220> FEATURE:
<221> NAME/KEY: modified_base
<222> LOCATION: (45)
<223> OTHER INFORMATION: a, c, t or g

<400> SEQUENCE: 9

```
aaccttacaa tcattatacc aactatcaaa atcataagac tcttnaactt ctgtttttga     60
tagttggtat aatgatttat gtattatctt aattcattat tattagtttc ggtcacaaa    119
```

<210> SEQ ID NO 10
<211> LENGTH: 60
<212> TYPE: PRT
<213> ORGANISM: Candida albicans

<400> SEQUENCE: 10

```
Met Ile Thr Asp Glu Gln Leu Asn Thr Ile Ala Leu Thr Phe Gly Phe
  1               5                  10                  15

Ala Ser Ile Ile Leu Ile Ile Ile Tyr His Ala Ile Ser Thr Asn Val
             20                  25                  30

His Lys Leu Glu Asp Glu Thr Pro Ser Ser Ser Phe Thr Arg Thr Asn
         35                  40                  45

Thr Thr Glu Thr Thr Val Ala Ser Lys Lys Lys Lys
     50                  55                  60
```

<210> SEQ ID NO 11
<211> LENGTH: 426

```
<212> TYPE: PRT
<213> ORGANISM: Candida albicans

<400> SEQUENCE: 11

Met Leu Lys Thr Leu Thr Gln Thr Leu Arg Leu Thr Gly Lys Ala Phe
 1               5                  10                  15

Pro Lys Val Arg Pro Ala Leu Ile Arg Thr Tyr Ala Ala Phe Asp Arg
            20                  25                  30

Ser Lys Pro His Val Asn Ile Gly Thr Ile Gly His Val Asp His Gly
        35                  40                  45

Lys Thr Thr Leu Thr Ala Ala Ile Thr Lys Val Leu Ala Glu Gln Gly
 50                  55                  60

Gly Ala Asn Phe Leu Asp Tyr Gly Ser Ile Asp Arg Ala Pro Glu Glu
 65                  70                  75                  80

Arg Ala Arg Gly Ile Thr Ile Ser Thr Ala His Val Glu Tyr Glu Thr
                85                  90                  95

Lys Asn Arg His Tyr Ala His Val Asp Cys Pro Gly His Ala Asp Tyr
            100                 105                 110

Ile Lys Asn Met Ile Thr Gly Ala Ala Gln Met Asp Gly Ala Ile Ile
        115                 120                 125

Val Val Ala Ala Thr Asp Gly Gln Met Pro Gln Thr Arg Glu His Leu
130                 135                 140

Leu Leu Ala Arg Gln Val Gly Val Gln Asp Leu Val Val Phe Val Asn
145                 150                 155                 160

Lys Val Asp Thr Ile Asp Asp Pro Glu Met Leu Glu Leu Val Glu Met
                165                 170                 175

Glu Met Arg Glu Leu Leu Ser Thr Tyr Gly Phe Asp Gly Asp Asn Thr
            180                 185                 190

Pro Val Ile Met Gly Ser Ala Leu Met Ala Leu Glu Asp Lys Lys Pro
        195                 200                 205

Glu Ile Gly Lys Glu Ala Ile Leu Lys Leu Leu Asp Ala Val Asp Glu
    210                 215                 220

His Ile Pro Thr Pro Ser Arg Asp Leu Glu Gln Pro Phe Leu Leu Pro
225                 230                 235                 240

Val Glu Asp Val Phe Ser Ile Ser Gly Arg Gly Thr Val Val Thr Gly
                245                 250                 255

Arg Val Glu Arg Gly Val Leu Lys Lys Gly Glu Glu Ile Glu Ile Val
            260                 265                 270

Gly Gly Phe Asp Lys Pro Tyr Lys Thr Thr Val Thr Gly Ile Glu Met
        275                 280                 285

Phe Lys Lys Glu Leu Asp Ser Ala Met Ala Gly Asp Asn Cys Gly Val
290                 295                 300

Leu Leu Arg Gly Val Lys Arg Asp Glu Ile Lys Arg Gly Met Val Leu
305                 310                 315                 320

Ala Lys Pro Gly Thr Ala Ser His Lys Lys Phe Leu Ala Ser Leu
                325                 330                 335

Tyr Ile Leu Thr Ser Glu Glu Gly Gly Arg Ser Thr Pro Phe Gly Glu
            340                 345                 350

Gly Tyr Lys Pro Gln Cys Phe Arg Thr Asn Asp Val Thr Thr Thr
        355                 360                 365

Phe Ser Phe Pro Glu Gly Glu Gly Val Asp His Ser Gln Met Ile Met
370                 375                 380

Pro Gly Asp Asn Ile Glu Met Val Gly Glu Leu Ile Lys Ser Cys Pro
385                 390                 395                 400
```

```
Leu Glu Val Asn Gln Arg Phe Asn Leu Arg Glu Gly Lys Thr Val
                405                 410                 415
Gly Thr Gly Leu Ile Thr Arg Ile Ile Glu
            420                 425

<210> SEQ ID NO 12
<211> LENGTH: 699
<212> TYPE: PRT
<213> ORGANISM: Candida albicans

<400> SEQUENCE: 12

Met Glu Val Thr Gln Arg Thr Gln Ser Gln Thr Gln Pro Thr Gln Gln
 1               5                  10                  15
Ser Pro Thr Thr Gln Thr Gln Thr Gln Ser Lys Glu Asp Gln Asn Arg
            20                  25                  30
Ile Cys Gln Leu Ile Cys Ser Thr Gly Gln Phe Gly Asn Tyr Asp Leu
        35                  40                  45
Asn Ile Asn Asp Lys Thr Ile Val Gln Gly Lys Met Thr Trp Tyr Phe
    50                  55                  60
Gly Arg Asp Pro Asn Ser Asp Leu Gln Val Ala Ser Ser Ser Arg Ile
65                  70                  75                  80
Ser Asn Lys His Phe Gln Ile Trp Leu Asn Phe Asn Asp Lys Ser Leu
                85                  90                  95
Trp Ile Lys Asp Thr Ser Thr Asn Gly Thr His Leu Asn Asn Ser Arg
            100                 105                 110
Leu Val Lys Gly Ser Asn Tyr Leu Leu Asn Gln Gly Asp Glu Ile Ala
        115                 120                 125
Val Gly Val Gly Arg Asp Glu Asp Val Val Arg Phe Val Val Val Phe
    130                 135                 140
Gly Asp Lys Tyr Asn Pro Ala Lys Leu Pro Asp Ser Thr Asn Thr Ile
145                 150                 155                 160
Lys Asp Glu Gly Ile Tyr Lys Asp Phe Ile Val Lys Asn Glu Thr Ile
                165                 170                 175
Gly Gln Gly Ala Phe Ala Thr Val Lys Lys Ala Ile Glu Arg Ser Thr
            180                 185                 190
Gly Glu Ser Tyr Ala Val Lys Ile Ile Asn Arg Arg Lys Ala Leu Asn
        195                 200                 205
Thr Gly Gly Gly Ser Ala Met Ala Gly Val Asp Arg Glu Leu Ser Ile
    210                 215                 220
Leu Glu Arg Leu Asn His Pro Asn Ile Val Ala Leu Lys Ala Phe Tyr
225                 230                 235                 240
Glu Asp Met Asp Asn Tyr Tyr Ile Val Met Glu Leu Val Pro Gly Gly
                245                 250                 255
Asp Leu Met Asp Phe Val Ala Ala Asn Gly Ala Ile Gly Glu Asp Ala
            260                 265                 270
Thr Gln Val Ile Thr Lys Gln Ile Leu Glu Gly Ile Ala Tyr Val His
        275                 280                 285
Asn Leu Gly Ile Ser His Arg Asp Leu Lys Pro Asp Asn Ile Leu Ile
    290                 295                 300
Met Gln Asp Asp Pro Ile Leu Val Lys Ile Thr Asp Phe Gly Leu Ala
305                 310                 315                 320
Lys Phe Ser Asp Asn Ser Thr Phe Met Lys Thr Phe Cys Gly Thr Leu
                325                 330                 335
Ala Tyr Val Ala Pro Glu Val Ile Thr Gly Lys Tyr Gly Ser Ser Gln
```

```
                    340                 345                 350
Met Glu Ser Gln Gln Lys Asp Asn Tyr Ser Ser Leu Val Asp Ile Trp
            355                 360                 365

Ser Leu Gly Cys Leu Val Tyr Val Leu Leu Thr Ser His Leu Pro Phe
    370                 375                 380

Asn Gly Lys Asn Gln Gln Gln Met Phe Ala Lys Ile Lys Arg Gly Glu
385                 390                 395                 400

Phe His Glu Ala Pro Leu Asn Ser Tyr Asp Ile Ser Glu Asp Gly Arg
                405                 410                 415

Asp Phe Leu Gln Cys Cys Leu Gln Val Asn Pro Lys Leu Arg Met Thr
            420                 425                 430

Ala Ala Glu Ala Leu Lys His Lys Trp Leu Gln Asp Leu Tyr Glu Glu
            435                 440                 445

Asp Ser Val Lys Ser Leu Ser Leu Ser Gln Ser Gln Ser Gln Gln Ser
        450                 455                 460

Arg Lys Ile Asp Asn Gly Ile His Ile Glu Ser Leu Ser Lys Ile Asp
465                 470                 475                 480

Glu Asp Val Met Leu Arg Pro Leu Asp Ser Glu Arg Asn Arg Lys Ser
                485                 490                 495

Ser Lys Gln Gln Asp Phe Lys Val Pro Lys Arg Val Ile Pro Leu Ser
            500                 505                 510

Gln His Pro Ala Thr Pro Leu Pro Met Ser Gln Pro Lys Lys Arg Pro
        515                 520                 525

Tyr Gln Ile Asp Pro Arg Thr Asn Lys Lys Val Asp Leu Glu Glu Pro
    530                 535                 540

Ser Thr Ser Lys Lys Val Lys Leu Ser Asp Ser Val Val Ala Glu Asp
545                 550                 555                 560

Tyr Leu Lys Leu Gly Pro Leu Ala Asn Ser Leu Phe Gln Glu Thr Ile
                565                 570                 575

Asn Ile Ser Lys Ser Pro Phe Ser Phe Gly Arg Asn Asp Thr Cys Asp
            580                 585                 590

Cys Glu Ile Asp Asp Asp Arg Leu Ser Lys Leu His Cys Val Ile Thr
        595                 600                 605

Lys Glu Asn Asp Ser Ile Trp Leu Leu Asp Lys Ser Thr Asn Ser Cys
    610                 615                 620

Leu Val Asn Asn Thr Ser Val Gly Lys Gly Asn Lys Val Leu Leu Arg
625                 630                 635                 640

Gly Gly Glu Ile Leu His Leu Phe Phe Asp Pro Leu Ser Ser Gln His
                645                 650                 655

Ile Gly Phe Lys Val Val Leu Val Asp Gln Ser Ser Gly Glu His Lys
            660                 665                 670

Ser Gln Val Glu Val Leu Lys Gln Thr Ser Glu Glu Met Asn Ile Ile
        675                 680                 685

Pro Leu Ile Ser Gly Leu Ser Ser Ile Ser Ser
    690                 695

<210> SEQ ID NO 13
<211> LENGTH: 295
<212> TYPE: PRT
<213> ORGANISM: Candida albicans

<400> SEQUENCE: 13

Met Gly Thr Ser Thr Ser Glu Ala Leu Lys Asn Ile Lys Asn Lys Gln
 1               5                  10                  15
```

```
Arg Arg Gln Lys Val Phe Ala Glu Ile Lys His Glu Lys Asn Lys Gln
            20                  25                  30

Arg His Lys Gln Arg Ala Glu Arg Ala Lys Glu Glu Arg Glu Asn Pro
        35                  40                  45

Glu Leu Arg Glu Arg Ile Ala Ala Asn Ile Pro Asp Thr Ile Asp
    50                  55                  60

Ser Lys Arg Ile Tyr Asp Glu Thr Ile Ala Ala Glu Val Gly Asp
65                  70                  75                  80

Asp Glu Phe Gln Ser Tyr Phe Thr Asn Leu Leu Glu Pro Lys Ile
                85                  90                  95

Leu Leu Thr Thr Ser Ala Asn Ala Lys Lys Pro Ala Tyr Glu Phe Ala
                100                 105                 110

Asp Met Ile Met Asp Phe Leu Pro Asn Val Thr Phe Ile Lys Arg Lys
            115                 120                 125

Lys Glu Tyr Thr Met Gln Asp Met Ala Lys Tyr Cys Ser Asn Arg Asp
130                 135                 140

Phe Thr Ala Leu Leu Val Ile Asn Glu Asp Lys Lys Val Asn Gly
145             150                 155                 160

Ile Thr Leu Ile Asn Leu Pro Glu Gly Pro Thr Phe Tyr Phe Ser Ile
                165                 170                 175

Thr Ser Ile Val Asp Gly Lys Arg Ile Lys Gly His Gly Lys Ala Gly
            180                 185                 190

Asp Tyr Leu Pro Glu Ile Val Leu Asn Asn Phe Asn Ser Arg Leu Gly
        195                 200                 205

Lys Thr Val Gly Arg Leu Phe Gln Ser Ile Phe Pro His Lys Pro Glu
        210                 215                 220

Leu Gln Gly Arg Gln Val Ile Thr Leu His Asn Gln Arg Asp Tyr Ile
225                 230                 235                 240

Phe Phe Arg Arg His Arg Tyr Ile Phe Arg Asn Glu Glu Lys Val Gly
                245                 250                 255

Leu Gln Glu Gly Pro Gln Phe Thr Leu Lys Leu Arg Arg Met Gln Lys
            260                 265                 270

Gly Val Arg Gly Asp Val Val Trp Glu His Arg Pro Asp Met Glu Arg
        275                 280                 285

Asp Lys Lys Lys Phe Tyr Leu
    290                 295

<210> SEQ ID NO 14
<211> LENGTH: 55
<212> TYPE: PRT
<213> ORGANISM: Candida albicans

<400> SEQUENCE: 14

Met Asn Ser Glu Lys Ile Ile Glu Val Ile Ile Ala Ile Phe Leu Pro
1               5                   10                  15

Pro Val Ala Val Phe Met Lys Cys Gly Ala Thr Thr Pro Leu Trp Ile
            20                  25                  30

Asn Leu Val Leu Cys Ile Phe Ile Trp Phe Pro Ala Ile Leu His Ala
        35                  40                  45

Leu Tyr Val Val Leu Lys Asp
    50                  55

<210> SEQ ID NO 15
<211> LENGTH: 773
<212> TYPE: PRT
<213> ORGANISM: Candida albicans
```

<400> SEQUENCE: 15

```
Met Thr Leu Gly Phe Asp Lys Phe Ile Ser Lys Val Ser Thr His Arg
 1               5                  10                  15

Arg Gln Ser Glu Pro Ser Ile Leu Glu Ile Ala Ala Thr Asn Ser Gln
            20                  25                  30

Asn Lys Ser Arg Arg Leu Ser Met Asp Asn Gly His Cys Tyr Val Arg
         35                  40                  45

Glu Ser Thr Asn Asn His His His Leu Asn Thr Val Asp Asn Leu
     50                  55                  60

Arg Gln Arg Ala Gly Ser Phe Ser Phe Ile Ser His His Asn His
 65                  70                  75                  80

His Gln Asn Ser His Asp Asn Tyr Thr Val Asp Pro Leu Thr Ser Asn
                 85                  90                  95

Gly Ala Arg Ile Ser Arg Ser Arg Ser Arg Ser Lys Ser Val Gly His
                100                 105                 110

Gly Glu Ala Ile Ser Pro Ala Tyr Phe Ser Lys Asn Lys Thr Lys Asp
            115                 120                 125

Leu Val Lys Gln Glu Thr Ala His Ile Ile Ser Lys Lys Leu Leu Asn
        130                 135                 140

Met Leu Gln Asp Leu Asp Leu Gln Asn Pro Ile Ala Leu Lys Thr Ile
145                 150                 155                 160

Ser Gln Gly Ser Glu Ser Lys Phe Cys Lys Ile Tyr Val Ser Asn Thr
                165                 170                 175

Asn Asn Cys Ile Tyr Leu Pro Ala Ala Ser Ser Thr Ser Phe Thr Tyr
            180                 185                 190

Glu Asp Asp Glu Asn Gly Gly Val Ile Ile Ala Glu Asp Arg Asn Asp
        195                 200                 205

Glu Met Pro Thr Ala Val Asn Asn Asn Thr Leu Ser Met Asp Ser Ile
210                 215                 220

Asn His Ser Glu Thr Asp Phe Ser Asp Ser Pro Pro Pro Asp Leu
225                 230                 235                 240

Phe Ser Lys Met Lys Ser Phe His Ser Pro Asn Tyr Leu Thr Ser Lys
                245                 250                 255

Ile Asp Ser Glu Cys Pro Ile Pro His Thr Phe Ala Val Ile Val Glu
            260                 265                 270

Leu Thr Lys Asp Ser Leu Ile Ile Lys Asp Leu His Phe Gln Phe Gln
        275                 280                 285

Ser Leu Thr Thr Ile Leu Trp Pro Thr Gly Asp Ala Tyr Asn Arg Thr
    290                 295                 300

His Ala Lys Glu Lys Phe Thr Ile Gly Asn Met Glu Trp Arg Thr Ser
305                 310                 315                 320

Leu Ser Asp Ala Asp Tyr Tyr Ile Asn Ser Ser Asn Ser Asn Asp Val
                325                 330                 335

Lys Ser Lys Asn Leu Gly Pro Glu Asp Leu Ile Asn Arg Thr Arg Glu
            340                 345                 350

Tyr Lys Leu Ile Asp Ile Glu Glu Pro Asn Asn Ser Ser Asn Ser Leu
        355                 360                 365

Ser Asp Asp Asp Met Asp Ile Asn Asn Ile Thr Ser Pro Leu Ser Thr
    370                 375                 380

Ser Pro Thr Ser Ser Ser Thr Ser Thr Asn Ser Thr Ser Asn Ser Leu
385                 390                 395                 400

Gly Ser Asp Ser Tyr Lys Ala Gly Leu Tyr Val Phe Leu Leu Pro Ile
```

```
                405                 410                 415
Leu Leu Pro Glu His Ile Pro Ala Ser Ile Val Ser Ile Asn Gly Ser
            420                 425                 430

Leu Ala His Thr Leu Ser Val Glu Cys Asn Lys Tyr Thr Asp Lys Leu
            435                 440                 445

Asn Arg Lys Ser Lys Val Ser Ala Ser Tyr Asn Leu Pro Met Val Arg
    450                 455                 460

Thr Pro Pro Asn Ile Gly Asn Ser Ile Ala Asp Lys Pro Ile Tyr Val
465                 470                 475                 480

Asn Arg Ile Trp Asn Asp Ala Val His Tyr Ile Ile Thr Phe Pro Arg
                485                 490                 495

Lys Tyr Val Thr Leu Gly Cys Glu His Met Ile Asn Val Lys Leu Ser
            500                 505                 510

Pro Met Val Lys Asp Val Val Ile Lys Arg Ile Lys Phe Asn Val Leu
            515                 520                 525

Glu Arg Ile Thr Tyr Val Ser Lys Asn Leu Ser Arg Glu Tyr Asp Tyr
    530                 535                 540

Asp Ser Glu Asp Pro Tyr Cys Ile His Pro Val Ser Lys Glu Asn Lys
545                 550                 555                 560

Val Arg Glu Arg Val Val Ser Leu Tyr Glu Leu Lys Thr Lys Ala Lys
                565                 570                 575

Gln Ser Ser Gly Gly His Leu Glu Ala Tyr Lys Gln Glu Val Met Lys
            580                 585                 590

Cys Pro Glu Asn Asn Leu Leu Phe Ser Cys Tyr Glu Val Glu Asn Asp
            595                 600                 605

Asn Asn Asn Gly Asn Gly Asn Gly Asn Gly Asn Gly Asn Lys Asn Val
    610                 615                 620

Lys Gln Lys Asn Lys Asp Gln Pro Met Ile Ala Thr Pro Leu Asp Ile
625                 630                 635                 640

Asn Val Ser Leu Pro Phe Leu Thr Thr Met Ser Asp Ser Leu Ile Met
                645                 650                 655

Thr Ser Ala Ile Glu Glu Gly Ser Asp Ser Pro His Thr Ser Arg
            660                 665                 670

Arg Gly Ser Ala Val Ser Met Thr Asp Asn Asn Thr Thr Pro Ser Asn
            675                 680                 685

Asn Asn Pro Leu Ser Pro Phe Leu Gly Ala Val Glu Thr Asn Gly Ala
    690                 695                 700

Ser Ile Asn Glu Ile Gly Asp His Thr Leu Phe Pro Asp Ser Asn Phe
705                 710                 715                 720

Arg His Ile Glu Ile Lys His Arg Leu Gln Val Thr Phe Arg Ile Ser
                725                 730                 735

Lys Pro Asp Ser Asp Asn Lys Met His His Tyr Glu Val Val Ile Asp
            740                 745                 750

Thr Pro Ile Val Leu Leu Ser Lys Cys Gln Glu Asp Ser Pro Pro
            755                 760                 765

Pro Tyr Ser Ser Val
    770

<210> SEQ ID NO 16
<211> LENGTH: 90
<212> TYPE: PRT
<213> ORGANISM: Candida albicans

<400> SEQUENCE: 16
```

```
Met Gly Glu Gly Thr Pro Ser Leu Gly Lys Arg His Asn Lys Ser His
 1               5                  10                  15

Thr Leu Cys Asn Arg Cys Gly Arg Arg Ser Phe His Val Gln Lys Lys
             20                  25                  30

Thr Cys Ser Ser Cys Gly Tyr Pro Ala Ala Lys Met Arg Ser His Asn
             35                  40                  45

Trp Ala Leu Lys Ala Lys Arg Arg Thr Thr Gly Thr Gly Arg Met
 50                  55                  60

Ala Tyr Leu Lys His Val Thr Arg Arg Phe Lys Asn Gly Phe Gln Thr
 65                  70                  75                  80

Gly Val Ala Lys Ala Gln Thr Pro Ser Ala
                 85                  90
```

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgcagctcga cctcgactg                                           19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgtgaatgt aagcgtgac                                           19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgagcagctc gccgtcgcgc                                          20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gagttatacc ctgcagctcg ac                                       22

<210> SEQ ID NO 21
<211> LENGTH: 6671
<212> TYPE: DNA
<213> ORGANISM: Artificial Sequence
<220> FEATURE:
<223> OTHER INFORMATION: Description of Artificial Sequence: Synthetic
      DNA plasmid

<400> SEQUENCE: 21

```
ttccatcggg gaaagtgggg gggaaaaaat tttaagcagt tcacaaaacc ttccaaaaaa      60
tatatggaca aagatgattg tattttcccg acaccaaaat cataattaat tatgagaaag     120
ttaaatgtaa cgttacaatt tatgtttatt tgaaggtgaa aagcgattta tgattttcc     180
gaaatgaaaa ttttttttag gtttattttt tttgtcgggc aaagaaaaac tgaacaagga     240
ttattaaaat ttttggtgtt tgtttgtgtc tggagaattc attcctctct catcttcaca     300
caatgtttag acatctgaca cgattcatga tagttcggtt tccggggttg gtgtttagtt     360
ttcgttttc ttttttttg gaaagaatgt tttagctcat tggttttctt tcttcattca     420
atagttttga aagaatttgc ccacttgtta ttacaatcat ataaaattaa actttgatat     480
aaaatagagt ttgaaagttt cccagatcct ttttgatttc tttgtaaatt ttttttctc     540
ccacatatac acacatacaa accgattttt ataagaaaga gttatacct gcagctcgac     600
ctcgactgtt taaacctgca ggcatgcaag cttggccaaa aaggcctcga ggaacatgac     660
caacaagtgt ctcctccaaa ttgctctcct gttgtgcttc tccactacag ctctttccat     720
gagctacaac ttgcttggat tcctacaaag aagcagcaat tttcagtgtc agaagctcct     780
gtggcaattg aatgggaggc ttgaatactg cctcaaggac aggatgaact ttgacatccc     840
tgaggagatt aagcagctgc agcagttcca aaggaggac gccgcattga ccatctatga     900
gatgctccag aacatctttg ctattttcag acaagattca tctagcactg gctggaatga     960
gactattgtt gagaacctcc tggctaatgt ctatcatcag ataaaccatc tgaagacagt    1020
cctgaagaa aaactggaga aagaagattt caccagggga aaactcatga gcagtctgca    1080
cctgaaaaga tattatggga ggattctgca ttacctgaag gccaaggagt acagtcactg    1140
tgcctggacc atagtcagag tggaaatcct aaggaacttt tacttcatta acagacttac    1200
aggttacctc cgaaactgaa gatctcctag cctgtgcctc tgggactgga caattgcttc    1260
aagcattctt caaccagcag atgctgttta agtgactgat ggctaatgta ctgcatatga    1320
aaggacacta gaagattttg aaattttat taaattatga gttattttta tttatttaaa    1380
ttttattttg gaaataaat tattttggt gcaaagtcc ctcgaggcct agcggccgcc    1440
tagaggatcc ccgggcgcta ggcggccgct aggccttttt ggccgaattc gagctcggta    1500
cccgggagga tccgtccccc tttctttg tcgatatcat gtaattagtt atgtcacgct    1560
tacattcacg ccctcccccc acatccgctc taaccgaaaa ggaaggagtt agacaacctg    1620
aagtctaggt ccctatttat tttttatag ttatgttagt attaagaacg ttatttatat    1680
ttcaaatttt tcttttttt ctgtacagac gcgtgtacgc atgtaacatt atactgaaaa    1740
ccttgcttga gaaggttttg ggacgctcga aggctttaat ttgcaagcta gcttggcgta    1800
atcatggtca tagctgtttc ctgtgtgaaa ttgttatccg ctcacaattc cacacaacat    1860
acgagccgga agcataaagt gtaaagcctg ggtgcctaa tgagtgagct aactcacatt    1920
aattgcgttg cgctcactgc ccgctttcca gtcgggaaac ctgtcgtgcc agagatctct    1980
gcattaatga atcggccaac gcgcggggag aggcggtttg cgtattgggc gctcttccgc    2040
ttcctcgctc actgactcgc tgcgctcggt cgttcggctg cggcgagcgg tatcagatcg    2100
atctcactca aaggcggtaa tacgttatc cacagaatca gggataacg caggaaagaa    2160
catgtgagca aaaggccagc aaaaggccag gaaccgtaaa aaggccgcgt tgctggcgtt    2220
tttccatagg ctccgccccc ctgacgagca tcacaaaaat cgacgctcaa gtcagaggtg    2280
gcgaaacccg acaggactat aaagatacca ggcgtttccc cctggaagct ccctcgtgcg    2340
```

-continued

```
ctctcctgtt ccgaccctgc cgcttaccgg atacctgtcc gcctttctcc cttcgggaag    2400
cgtggcgctt tctcatagct cacgctgtag gtatctcagt tcggtgtagg tcgttcgctc    2460
caagctgggc tgtgtgcacg aaccccccgt tcagcccgac cgctgcgcct tatccggtaa    2520
ctatcgtctt gagtccaacc cggtaagaca cgacttatcg ccactggcag cagccactgg    2580
taacaggatt agcagagcga ggtatgtagg cggtgctaca gagttcttga agtggtggcc    2640
taactacggc tacactagaa ggacagtatt tggtatctgc gctctgctga agccagttac    2700
cttcggaaaa agagttggta gctcttgatc cggcaaacaa accaccgctg gtagcggtgg    2760
tttttttgtt tgcaagcagc agattacgcg cagaaaaaaa ggatctcaag aagatccttt    2820
gatcttttct acggggtctg acgctcagtg gaacgaaaac tcacgttaag ggattttggt    2880
catgagatta tcaaaaagga tcttcaccta gatcctttta aattaaaaat gaagttttaa    2940
atcaatctaa agaagtggat ctaggaaaat ttaattttta cttcaaaatt tagttagatt    3000
agtatatatg agtaaacttg gtctgacagt taccaatgct taatcagtga ggcacctatc    3060
tcagcgatct gtctatttcg ttcatccata gttgcctgac tccccgtcgt gtagataact    3120
acgatacggg agggcttacc atctggcccc agtgctgcaa tgataccgcg agacccacgc    3180
tcaccggctc cagatttatc agcaataaac cagccagccg aagggccga gcgcagaagt    3240 ggtcctgcaa ctttatccgc ctccatccag tctattaatt gttgccggga agctagagta    3300
agtagttcgc cagttaatag tttgcgcaac gttgttgcca ttgctacagg catcgtggtg    3360
tcacgctcgt cgtttggtat ggcttcattc agctccggtt cccaacgatc aaggcgagtt    3420
acatgatccc ccatgttgtg caaaaaagcg gttagctcct tcggtcctcc gatcgttgtc    3480
agaagtaagt tggccgcagt gttatcactc atggttatgg cagcactgca taattctctt    3540
actgtcatgc catccgtaag atgcttttct gtgactggtg agtactcaac caagtcattc    3600
tgagaatagt gtatgcggcg accgagttgc tcttgcccgg cgtcaatacg ggataatacc    3660
gcgccacata gcagaacttt aaaagtgctc atcattggaa aacgttcttc ggggcgaaaa    3720
ctctcaagga tcttaccgct gttgagatcc agttcgatgt aacccactcg tgcacccaac    3780
tgatcttcag catcttttac tttcaccagc gtttctgggt gagcaaaaac aggaaggcaa    3840
aatgccgcaa aaaagggaat aagggcgaca cggaaatgtt gaatactcat actcttcctt    3900
tttcaatatt attgaagcat ttatcagggt tattgtctca tgagcggata catatttgaa    3960
tgtatttaga aaataaaca aatagggggtt ccgcgcacat ttccccgaaa agtgccacct    4020
gacgtctaag aaaccattat tatcatgaca ttaacctata aaaataggcg tatcacgagg    4080
ccctttcgtc tcgcgcgttt cggtgatgac ggtgaaaacc tctgacacat gcagctcccg    4140
gagacggtca cagcttgtct gtaagcggat gccgggagca gacaagcccg tcagggcgcg    4200
tcagcgggtg ttggcgggtg tcggggctgg cttaactatg cggcatcaga gcagattgta    4260
ctgagagtgc accatatcga cgctctccct tatgcgactc ctgcattagg aagcagccca    4320
gtagtaggtt gaggccgttg agcaccgccg ccgcaaggaa tggtgcatgc aaggagatgg    4380
cgcccaacag tcccccggcc acgggccctg ccaccatacc cacgccgaaa caagcactaa    4440
taggaattga tttggatggt ataaacggaa acaaaaaaaa gagctggtac tactttcttt    4500
aaaattattt tattatttga ttttatttaa tagtatatat tatatttga acgtagatta    4560 ttttgttgaa agttgctgta gtgccattga ttcgtaacac taattctgta ttagtcattc    4620
ctcttgtttg atagtatcca aaaaacggc tattttttg caatcttatt tcctgcatat    4680
```

-continued

```
tatacagata acataatgaa agaaaaaatc ttttttttg ttcttcaatg atgatttcaa      4740
ccattctttt aaacattgat caattcctga gcaacaaccc catacacact ggtttatata      4800
ccgccccttt tacagttgaa gaaagaaata gaaatagaaa tagcaaacaa aagatatgac      4860
agtcaacact aagacctata gtgagagagc agaaactcat gcctcaccag tagcacagcg      4920
attatttcga ttaatggaac tgaagaaaac caatttatgt gcatcaattg acgttgatac      4980
cactaaggag ttcctcgagt taattgataa attaggtcct tatgtatgct taatcaagac      5040
tcatattgat ataatcaatg attttttccta tgaatccact attgaaccat tattagaact      5100
ttcacgtaaa catcaattta tgattttttga agatagaaaa tttgctgata ttggtaatac      5160
cgtaaagaaa caatatattg gtggagttta taaaattagt agttgggcag atattaccaa      5220
tgctcatggt gtcactggga atggagtggt tgaaggatta aaacagggag ctaaagaaac      5280
caccaccaac caagagccaa gagggttatt gatgttagct gaattatcat cagtgggatc      5340
attagcatat ggagaatatt ctcaaaaaac tgttgaaatt gctaaatccg ataaggaatt      5400
tgttattgga tttattgccc aacgtgatat gggtggccaa gaagaaggat ttgattggct      5460
tattatgaca cctggagttg gattagatga taaaggtgat ggattaggac aacaatatag      5520
aactgttgat gaagttgtta gcactggaac tgatattatc attgttggta gaggattgtt      5580
tggtaaagga agagatccag atattgaagg taaaaggtat agaaatgctg gttggaatgc      5640
ttatttgaaa aagactggcc aattataaat gtgaaggggg agattttcac tttattagat      5700
ttgtatatat gtagaataaa taaataaata agttaaataa ataattaaat aagggtggta      5760
attattacta tttacaatca aaggtggtcc ttctagctgt aatccgggca gcgcaacgga      5820
acattcatca gtgtaaaaat ggaatcaata aagccctgcg ctcatgagcc cgaagtggcg      5880
agcccgatct tccccatcgg tgatgtcggc gatataggcg ccagcaaccg cacctgtggc      5940
gccgcagcgc gcagggtcag cctgaatacg cgtttaatga ccagcacagt cgtgatggca      6000
aggtcagaat agcccaagtc ggccgagggg cctgtacagt gagggaagat ctgatattga      6060
cgaagaggaa ccaatgtaac gttacactga agaaaacaca caataaacgg gaagaaacgg      6120
tgtaaaagtg tgaaaataat ttttgaatat catttcccctt ggtttaattc caaacgaaac      6180 gtgtttttt tagagaatgg gaattcttat tggatgtcta gattgtttgt ttactccaga      6240
ctgtgcacaa aaacgtttgg atggatgatc agaagatatt tttaggctta gctctaaata      6300
taagaaatga tgcttgaaaa accagacaga aattgagttt caaaaattgg taatgtgagg      6360
tattagtcaa ctaaccaaat aacaatgcaa accggttgat acatttcatt ttgaaaataa      6420
tgaaactgga attggatgac cagcacacaa acacataaag taattatggg aattagaagc      6480
gaacatagag gagtacttgg ccacgaacag aatacaagtg ggaacactat tttctccatt      6540
gttttagttc tgttttttg tcagcctagt tttgtgctat gtgtaaaaaa tattgccaag      6600
aaaaaaagct tgttttgtgg ccagtgtccg aaaaaaattt tggggaatct tcggattaat      6660 ttatgtttc a                                                            6671
```

<210> SEQ ID NO 22
<211> LENGTH: 7127
<212> TYPE: DNA
<213> ORGANISM: Artificial Sequence
<220> FEATURE:
<223> OTHER INFORMATION: Description of Artificial Sequence: Synthetic
      DNA plasmid

<400> SEQUENCE: 22

| | |
|---|---|
| agcttgagta ttctatagtg tcacctaaat agcttggcgt aatcatggtc atagctgttt | 60 |
| cctgtgtgaa attgttatcc gctcacaatt ccacacaaca tacgagccgg aagcataaag | 120 |
| tgtaaagcct ggggtgccta atgagtgagc taactcacat taattgcgtt gcgctcactg | 180 |
| cccgctttcc agtcgggaaa cctgtcgtgc cagctgcatt aatgaatcgg ccaacgcgcg | 240 |
| gggagaggcg gtttgcgtat tgggcgctct tccgcttcct cgctcactga ctcgctgcgc | 300 |
| tcggtcgttc ggctgcggcg agcggtatca gctcactcaa aggcggtaat acggttatcc | 360 |
| acagaatcag gggataacgc aggaaagaac atgtgagcaa aaggccagca aaaggccagg | 420 |
| aaccgtaaaa aggccgcgtt gctggcgttt ttccataggc tccgcccccc tgacgagcat | 480 |
| cacaaaaatc gacgctcaag tcagaggtgg cgaaacccga caggactata agataccag | 540 |
| gcgtttcccc ctggaagctc cctcgtgcgc tctcctgttc cgaccctgcc gcttaccgga | 600 |
| tacctgtccg cctttctccc ttcgggaagc gtggcgcttt ctcatagctc acgctgtagg | 660 |
| tatctcagtt cggtgtaggt cgttcgctcc aagctgggct gtgtgcacga accccccgtt | 720 |
| cagcccgacc gctgcgcctt atccggtaac tatcgtcttg agtccaaccc ggtaagacac | 780 |
| gacttatcgc cactggcagc agccactggt aacaggatta gcagagcgag gtatgtaggc | 840 |
| ggtgctacag agttcttgaa gtggtggcct aactacggct acactagaag gacagtattt | 900 |
| ggtatctgcg ctctgctgaa gccagttacc ttcggaaaaa gagttggtag ctcttgatcc | 960 |
| ggcaaacaaa ccaccgctgg tagcggtggt ttttttgttt gcaagcagca gattacgcgc | 1020 |
| agaaaaaaag gatctcaaga agatcctttg atcttttcta cggggtctga cgctcagtgg | 1080 |
| aacgaaaact cacgttaagg gattttggtc atgagattat caaaaaggat cttcacctag | 1140 |
| atccttttaa attaaaaatg aagttttaaa tcaatctaaa gtatatatga gtaaacttgg | 1200 |
| tctgacagtt accaatgctt aatcagtgag gcacctatct cagcgatctg tctatttcgt | 1260 |
| tcatccatag ttgcctgact ccccgtcgtg tagataacta cccacgct caccggctcc | 1320 |
| agatttatca gcaataaacc agccagccgg aagggccgag cgcagaagtg gtcctgcaac | 1380 |
| tttatccgcc tccatccagt ctattaattg ttgccgggaa gctagagtaa gtagttcgcc | 1440 |
| agttaatagt ttgcgcaacg ttgttgccat tgctacaggc atcgtggtgt cacgctcgtc | 1500 |
| gtttggtatg gcttcattca gctccggttc ccaacgatca aggcgagtta catgatcccc | 1560 |
| catgttgtgc aaaaaagcgg ttagctcctt cggtcctccg atcgttgtca gaagtaagtt | 1620 |
| ggccgcagtg ttatcactca tggttatggc agcactgcat aattctctta ctgtcatgcc | 1680 |
| atccgtaaga tgcttttctg tgactggtga gtactcaacc aagtcattct gagaatagtg | 1740 |
| tatgcggcga ccgagttgct cttgcccggc gtcaatacgg gataataccg cgccacatag | 1800 |
| cagaacttta aaagtgctca tcattggaaa acgttcttcg gggcgaaaac tctcaaggat | 1860 |
| cttaccgctg ttgagatcca gttcgatgta acccactcgt gcacccaact gatcttcagc | 1920 |
| atcttttact ttcaccagcg tttctgggtg agcaaaaaca ggaaggcaaa atgccgcaaa | 1980 |
| aaagggaata agggcgacac ggaaatgttg aatactcata ctcttccttt ttcaatatta | 2040 |
| ttgaagcatt tatcagggtt attgtctcat gagcggatac atatttgaat gtatttagaa | 2100 |
| aaataaacaa ataggggttc cgcgcacatt tccccgaaaa gtgccacctg acgtctaaga | 2160 |
| aaccattatt atcatgacat taacctataa aaataggcgt atcacgaggc ctttcgtct | 2220 |
| cgcgcgtttc ggtgatgacg gtgaaaacct ctgacacatg cagctcccgg agacggtcac | 2280 |
| agcttgtctg taagcggatg ccgggagcag acaagcccgt cagggcgcgt cagcgggtgt | 2340 |
| tggcgggtgt cggggctggc ttaactatgc ggcatcagag cagattgtac tgagagtgca | 2400 |

-continued

```
ccatatgcgg tgtgaaatac cgcacagatg cgtaaggaga aaataccgca tcaggcgaaa      2460
ttgtaaacgt taatattttg ttaaaattcg cgttaaatat ttgttaaatc agctcatttt      2520
ttaaccaata ggccgaaatc ggcaaaatcc cttataaatc aaaagaatag accgagatag      2580
ggttgagtgt tgttccagtt tggaacaaga gtccactatt aaagaacgtg gactccaacg      2640
tcaaagggcg aaaaaccgtc tatcagggcg atggcccact acgtgaacca tcacccaaat      2700
caagttttt gcggtcgagg tgccgtaaag ctctaaatcg gaaccctaaa gggagccccc       2760
gatttagagc ttgacgggga agccggcga acgtggcgag aaaggaaggg aagaaagcga       2820
aaggagcggg cgctagggcg ctggcaagtg tagcggtcac gctgcgcgta accaccacac      2880
ccgccgcgct taatgcgccg ctacaggcg cgtccattcg ccattcaggc tgcgcaactg       2940
ttgggaaggg cgatcggtgc gggcctcttc gctattacgc cagctggcga aggggatg       3000
tgctgcaagg cgattaagtt gggtaacgcc agggttttcc cagtcacgac gttgtaaaac      3060
gacggccagt gaattgtaat acgactcact ataggcgaa ttggttttcc aatgatgagc      3120
acttttaaag ttctgctatg tggcgcggta ttatcccgtg ttgacgccgg gcaagagcaa     3180
ctcggtcgcc gcatacacta ttctcagaat gacttggttg agtactaata ggaattgatt    3240
tggatggtat aaacgaaac aaaaaaaaga gctggtacta ctttcttaa aattatttta       3300
ttatttgatt ttatttaata gtatatatta tattttgaac gtagattatt ttgttgaaag     3360
ttgctgtagt gccattgatt cgtaacacta attctgtatt agtcattcct cttgtttgat    3420
agtatccaaa aaacggcta tttttttgca atcttatttc ctgcatatta tacagataac     3480
ataatgaaag aaaaaatctt tttttttgtt cttcaatgat gatttcaacc attcttttaa     3540
acattgatca attcctgagc aacaacccca tacacactgg tttatatacc gccccttta      3600
cagttgaaga aagaaataga aatagaaata gcaaacaaaa gatatgacag tcaacactaa     3660
gacctatagt gagagagcag aaactcatgc ctcaccagta gcacagcgat tatttcgatt     3720
aatggaactg aagaaaacca atttatgtgc atcaattgac gttgatacca ctaaggaatt     3780
ccttgaatta attgataaat taggtcctta tgtatgctta atcaagactc atattgatat      3840
aatcaatgat ttttcctatg aatccactat tgaaccatta ttagaacttt cacgtaaaca      3900
tcaatttatg atttttgaag atagaaaatt tgctgtatat tggtaataccg taaagaaaca     3960
atatattggt ggagtttata aaattagtag ttgggcagat attaccaatg ctcatggtgt     4020
cactgggaat ggagtggttg aaggattaaa acagggagct aaagaaacca ccaccaacca     4080
agagccaaga gggttattga tgttagctga attatcatca gtgggatcat tagcatatgg     4140
agaatattct caaaaaactg ttgaaattgc taaatccgat aaggaatttg ttattggatt     4200
tattgcccaa cgtgatatgg gtggccaaga agaaggattt gattggctta ttatgacacc    4260
tggagttgga ttagatgata aggtgatgg attaggacaa caatatagaa ctgttgatga      4320
agttgttagc actggaactg atattatcat tgttggtaga ggattgtttg gtaaaggaag     4380
agatccagat attgaaggta aaggtatag aaatgctggt tggaatgctt atttgaaaaa     4440
gactggccaa ttataaatgt gaagggggag attttcactt tattagattt gtatatatgt     4500
agaataaata aataaataag ttaaataaat aattaaataa gggtggtaat tattactatt     4560
tacaatcaaa ggtggtcctt ctagctgtaa tccgggcagc gcaacggaac attcatcagt     4620
gtaaaaatgg aatcaataaa gccctgcgca gcgcgcaggg tcagcctgaa tacgcgttta    4680
atgaccagca cagtcgtgat ggcaaggtca gaatagccca agtcggccga ggggcctgta    4740
```

```
cagtgaggga agatctgata ttgacgaaga ggaaccaatg taacgttaca ctgaagaaaa    4800
cacataataa acgggaagaa acggtgtaaa agtgtgaaaa taatttttga atatcatttc    4860
ccttggttta attccaaacg aaacgtgtat ttttttagag aatgggaatt cttattggat    4920
gtctagattg tttgtttact ccagactgtg cacaaaaacg tttggatgga tgatcagaag    4980
atatttttag gcttagctct aaatataaga aatgatgctt gaaatccag acagaaattg     5040 agtttcaaaa attggtaatg tgaggtatta gtcaactaac caaataacaa tgcaaaccgg    5100
ttgatacatt tcattttgaa ataatgaaa ctggaattgg atgaccagca cacaaacaca     5160
taaagtaatt atgggaatta aagcgaaca tagaggaata ctttgccacg aacagaatac     5220
aagtgggaac acttttttct ccattgtttt agttctgttt ttttgtcaaa ctggttttgt    5280
gctatgtgta aaaaaatatt gccaagaaaa aaagcttgtt ttgtggccag tgtccgaaaa    5340
aaatttgggg gaagcttcgg attaatttat ttttttattc catcgggaa agtgggggg      5400 aaaaaaatt taagcagttc ataaaacctt ccaaaaaata tatggacaga gatgattgta    5460
ttttcccgac accaaaatca taattaacta tgagaaaatt gaatgtaacg ttacaattta    5520
tttttatttg aagctgaaaa gcgatttatg attttttccga aatgaaaatt ttttttaggt   5580 ttatttttt tgtcgggcaa agaaaaactg aacaaggatt attaaaattt ttggtgtttg     5640
tttgtgtctg gagaattcat tcctctctca tcttcacaca atgtttagac atctgacacg    5700
attcaaaata gttcggtttc cggggttggt gtttagtttt cgttttttcgt ttttttttgga 5760 aagaatgttt tagctcattg gttttctttc ttcattcaat agttttgaaa gaatttgccc    5820
acttgttatt acaatcatat aaaattaaac tttgatataa aatagagttt gaaagtttcc    5880
cagatccttt tgatttctt tgtaattttt ttttctccca catatacaca catacaaacc     5940 gattttata agaaagagtt ataccctgca gctcgacctc gagggatccg ggccctctag    6000
atgcggccgc taggcctcga gggacttttg caccaaaaat aatttatttt ccaaaataaa   6060
atttaaataa ataaaaataa ctcataattt aataaaaatt tcaaaatctt ctagtgtcct   6120
ttcatatgca gtacattagc catcagtcac ttaaacagca tctgctggtt gaagaatgct   6180
tgaagcaatt gtccagtccc agaggcacag gctaggagat cttcagtttc ggaggtaacc   6240
tgtaagtctg ttaatgaagt aaaagttcct taggatttcc actctgacta tggtccaggc   6300
acagtgactg tactccttgg ccttcaggta atgcagaatc ctcccataat atctttttcag 6360 gtgcagactg ctcatgagtt ttcccctggt gaaatcttct ttctccagtt tttcttccag   6420
gactgtcttc agatggttta tctgatgata gacattagcc aggaggttct caacaatagt   6480
ctcattccag ccagtgctag atgaatcttg tctgaaaata gcaaagatgt tctggagcat   6540
ctcatagatg gtcaatgcgg cgtcctcctt ctggaactgc tgcagctgct taatctcctc   6600
agggatgtca aagttcatcc tgtccttgag gcagtattca agcctcccat tcaattgcca   6660
caggagcttc tgacactgaa aattgctgct tctttgtagg aatccaagca agttgtagct   6720
catggaaaga gctgtagtgg agaagcacaa caggagagca atttggagga gacacttgtt   6780
ggtcatgttc ctcgaggcct ttttggccag ctggcgcctg ctgcgcgacg gcgagctgct   6840
caccacccag gatccgtccc ccttttcctt tgtcgatatc atgtaattag ttatgtcacg   6900
cttacattca cgccctcccc ccacatccgc tctaaccgaa aaggaaggag ttagacaacc   6960
tgaagtctag gtccctattt attttttat agttatgtta gtattaagaa cgttatttat    7020
atttcaaatt tttctttttt ttctgtacag acgcgtgtac gcatgtaaca ttatactgaa    7080
aaccttgctt gagaaggttt tgggacgctc gaaggcttta atttgca                 7127
```

```
<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gttggccttt t                                                           11

<210> SEQ ID NO 24
<211> LENGTH: 8
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24 aggccaac                                                                8
```

DRUG TARGETS IN *CANDIDA ALBICANS*

CROSS REFERENCE TO RELATED APPLICATIONS

This application is a National Stage application under 35 U.S.C. § 371 of International Application No. PCT/EP99/09833 filed 6 Dec. 1999, which claims priority from EP98204122.0, filed 4 Dec. 1998, the contents of which are hereby incorporated by reference.

FIELD OF THE INVENTION

The present invention is concerned with the identification of genes or functional fragments thereof from *Candida albicans* which are critical for growth and cell division and which genes may be used as selective drug targets to treat *Candida albicans* associated infections. Novel nucleic acid sequences from *Candida albicans* are also provided and which encode the polypeptides, which are critical for growth of *Candida albicans*.

BACKGROUND OF THE INVENTION

Opportunistic infections in immunocompromised hosts represent an increasingly common cause of mortality and morbidity. *Candida* species are among the most commonly identified fungal pathogens associated with such opportunistic infections, with *Candida albicans* being the most common species. Such fungal infections are thus problematical in, for example, AIDS populations in addition to normal healthy women where *Candida albicans* yeasts represent the most common cause of vulvovaginitis.

Although compounds do exist for treating such disorders, such as, amphotericin, these drugs are generally limited in their treatment because of their toxicity and side effects. Therefore, there exists a need for new compounds, which may be used to treat *Candida* associated infections in addition to compounds, which are selective in their action against *Candida albicans*.

Classical approaches for identifying anti-fungal compounds have relied almost exclusively on inhibition of fungal or yeast growth as an endpoint. Libraries of natural products, semi-synthetic, or synthetic chemicals are screened for their ability to kill or arrest growth of the target pathogen or a related nonpathogenic model organism. These tests are cumbersome and provide no information about a compounds mechanism of action. The promising lead compounds that emerge from such screens must then be tested for possible host-toxicity and detailed mechanism of action studies must subsequently be conducted to identify the affected molecular target.

SUMMARY OF THE INVENTION

The present inventors have now identified a range of nucleic acid sequences from *Candida albicans*, which encode polypeptides, which are critical for its survival and growth. These sequences represent novel targets which can be incorporated into an assay to selectively identify compounds capable of inhibiting expression of such polypeptides and their potential use in alleviating diseases or conditions associated with *Candida albicans* infection.

In a first aspect of the invention, the invention relates to a nucleic acid molecule encoding a polypeptide which is critical for survival and growth of the yeast *Candida albicans* and which nucleic acid molecule is selected from the group consisting of SEQ ID NO: 1 to SEQ ID NO: 9. More preferably where nucleic acid molecule is selected from the group consisting of SEQ ID NO: 1 to SEQ ID NO: 3 and still more preferably consisting of SEQ ID NO:1 and SEQ ID NO:2.

In a preferred embodiment of this aspect of the invention, the nucleic acid molecule is either RNA or DNA, and in one embodiment, cDNA. The invention also relates to a first nucleic acid molecule capable of hybridising to a second nucleic acid molecule encoding a polypeptide which is critical for survival and growth of the yeast *Candida albicans* and which second nucleic acid molecule is selected from the group consisting of SEQ ID NO: 1 to SEQ ID NO: 9 under high stringency conditions. In yet another embodiment, the invention relates to an antisense molecule comprising a first nucleic acid molecule capable of hybridising to a second nucleic acid molecule encoding a polypeptide which is critical for survival and growth of the yeast *Candida albicans* wherein the second nucleic acid molecule is selected from the group consisting of SEQ ID NO: 1 to SEQ ID NO: 9.

The invention also relates to cells containing a nucleic acid molecule encoding a polypeptide which is critical for survival and growth of the yeast *Candida albicans* and which nucleic acid molecule is selected from the group consisting of SEQ ID NO: 1 to SEQ ID NO: 9, wherein said cells are bacterial or eukaryotic. The invention further relates to polypeptide encoded by a nucleic acid molecule which is critical for survival and growth of the yeast *Candida albicans* and which nucleic acid molecule is selected from the group consisting of SEQ ID NO: 1 to SEQ ID NO: 9 and to polypeptide having any of amino acid sequences selected from the group consisting of SEQ ID NO: 10 to SEQ ID NO: 16.

The invention also relates to a recombinant DNA construct comprising a nucleic acid molecule encoding a polypeptide which is critical for survival and growth of the yeast *Candida albicans* and which nucleic acid molecule is selected from the group consisting of SEQ ID NO: 1 to SEQ ID NO: 9, wherein the nucleic acid molecule is DNA. Preferably the DNA is an expression vector and preferably the expression vector includes an inducible promoter and/or a reporter molecule. The invention also relates to recombinant DNA constructs comprising a first nucleic acid molecule wherein the first nucleic acid molecule or a molecule complementary to the first nucleic acid molecule is capable of hybridising to a second nucleic acid molecule encoding a polypeptide which is critical for survival and growth of the yeast *Candida albicans* and which second nucleic acid molecule is selected from the group consisting of SEQ ID NO: 1 to SEQ ID NO: 9 wherein the first nucleic acid molecule is inserted in the antisense orientation.

The invention also relates to cells containing a recombinant DNA construct comprising a nucleic acid molecule encoding a polypeptide which is critical for survival and growth of the yeast *Candida albicans* and which nucleic acid molecule is selected from the group consisting of SEQ ID NO: 1 to SEQ ID NO: 9, wherein said cells are bacterial or eukaryotic.

In another aspect of this invention, the nucleic acid molecules or polypeptides of this invention are provided in a pharmaceutically acceptable carrier, diluent or excipient.

The invention further relates to a method for treating a *Candida albicans*-associated disease comprising the step of: administering a composition of matter comprising an antisense nucleic acid molecule capable of binding to a *Candida* albicans-originating nucleic acid sequence selected from the group consisting of SEQ ID NO:1 to SEQ ID NO:9.

In another aspect of this invention, the invention relates to a *Candida albicans* cell comprising an induced mutation in the DNA sequence encoding a polypeptide which is critical for survival and growth of the yeast *Candida albicans* wherein the polypeptide is encoded by a nucleic acid molecule is selected from the group consisting of SEQ ID NO: 1 to SEQ ID NO: 9.

The invention also relates to a method of identifying compounds which selectively modulate expression or functionality of polypeptides or metabolic pathways in which these polypeptides are involved and which polypeptides are crucial for growth and survival of *Candida albicans*, which method comprises: contacting a compound to be tested with one or more *Candida albicans* cells having a mutation in a nucleic acid molecule, the nucleic acid molecule encoding a polypeptide which is critical for survival and growth of the yeast *Candida albicans* and which nucleic acid molecule is selected from the group consisting of SEQ ID NO: 1 to SEQ ID NO: 9 wherein the mutation results in overexpression or underexpression of said polypeptide in addition to contacting one or more wild type *Candida albicans* cells with said compound; and monitoring the growth and/or activity of said mutated cell compared to said wild type; wherein differential growth or activity of said one or more mutated *Candida* cells is indicative of selective action of said compound on a polypeptide or another polypeptide in the same or a parallel pathway. The invention further relates to compounds identified by this method. The compounds can be provided in a pharmaceutical composition with a pharmaceutically acceptable carrier, diluent or excipient therefor.

The invention also relates to a method of identifying DNA sequences from a cell or organism which DNA encodes polypeptides which are critical for growth or survival of said cell or organism, which method comprises: preparing a cDNA or genomic library from said cell or organism in a suitable expression vector which vector is such that it can either integrate into the genome in said cell or that it permits transcription of antisense RNA from the nucleotide sequences in said cDNA or genomic library; selecting transformants exhibiting impaired growth and determining the nucleotide sequence of the cDNA or genomic sequence from the library included in the vector from said transformant. In a preferred aspect of this invention, the cell or organism is a yeast or filamentous fungus and more preferably the cell or organism is any of *Saccharomyces cerevisiae, Schizosaccharomyces pombe* or *Candida albicans*.

The invention further relates to antibody capable of specifically binding to a polypeptide of this invention. The invention also relates to oligonucleotides comprising a fragment of from 10 to 120 contiguous nucleotides of a nucleic acid molecule encoding a polypeptide which is critical for survival and growth of the yeast *Candida albicans* and which nucleic acid molecule is selected from the group consisting of SEQ ID NO: 1 to SEQ ID NO: 9.

Preferably the oligonucleotide comprises a fragment of from 10 to 50 contiguous nucleotides.

DETAILED DESCRIPTION OF THE INVENTION

Figure 1:
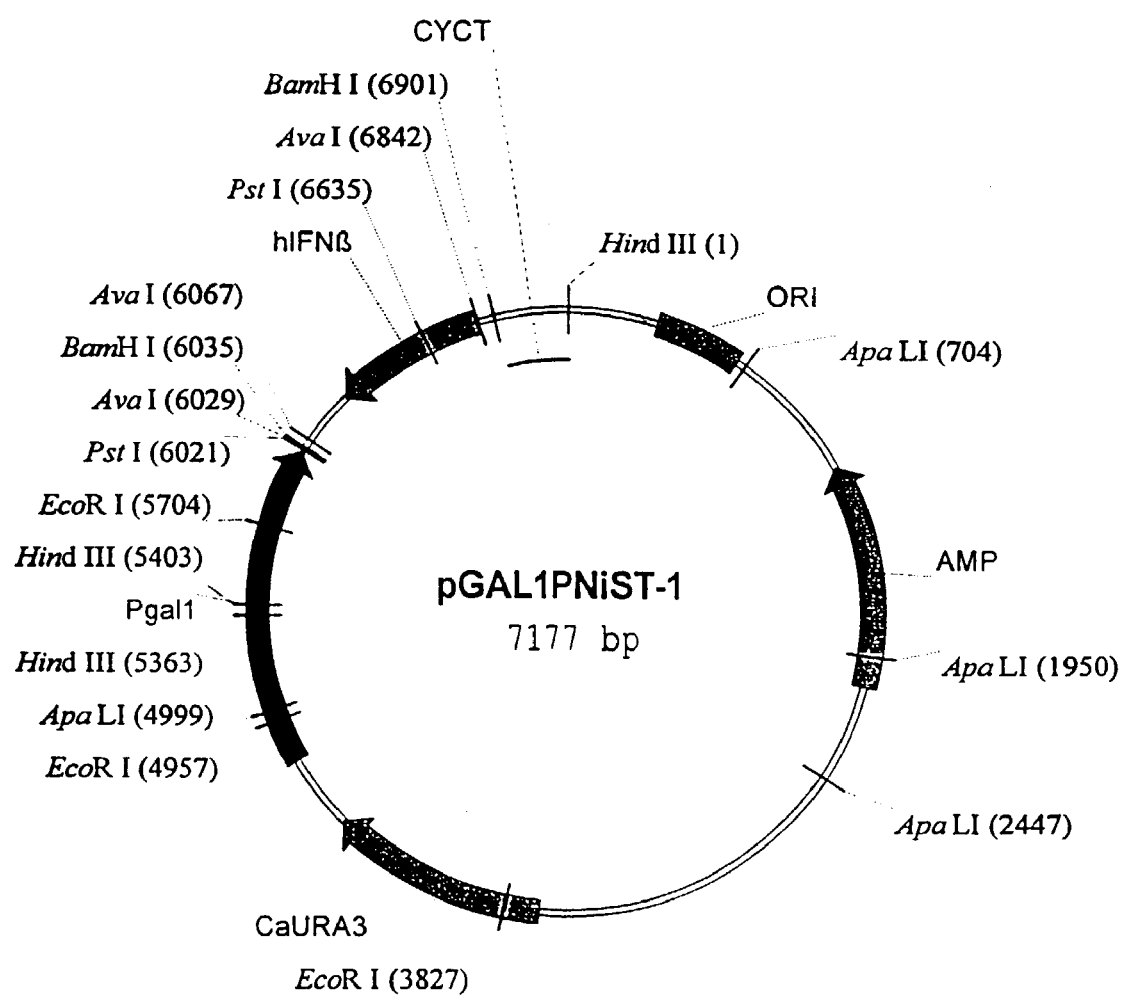
FIG. 1 is a diagrammatic representation of plasmid pGAL1PNiST-1.
Figure 2:
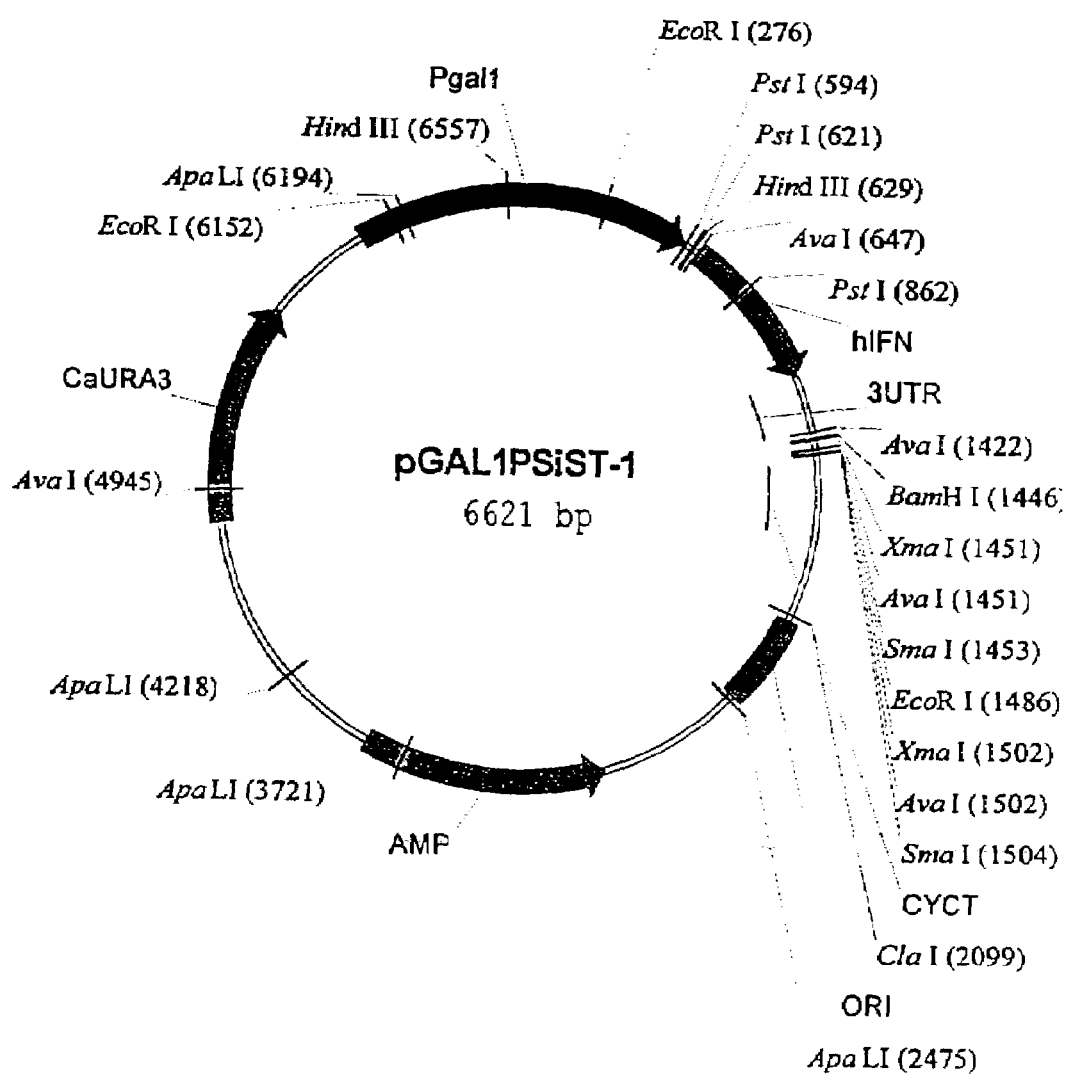
FIG. 2 is a diagrammatic representation of plasmid pGAL1PSiST-1.
Figure 3:
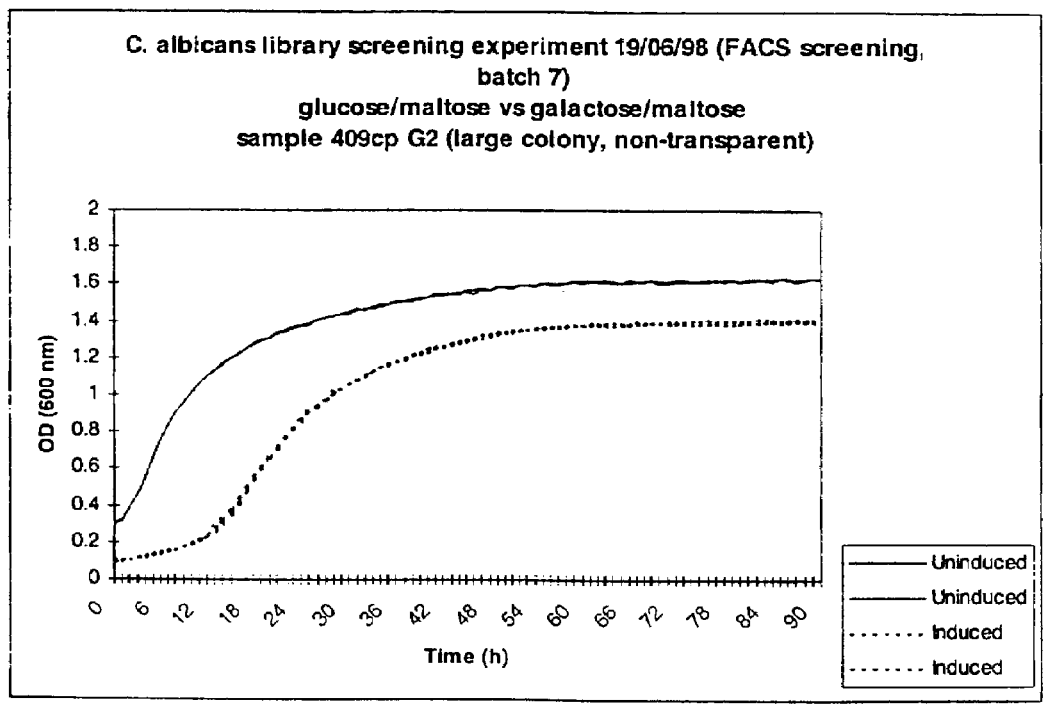
FIG. 3 is an exemplary growth curve of a *Candida albicans* strain demonstrating antisense-induced reduction in growth in response to intracellular antisense expressing specifically targeting one of the nucleic acid sequences of this invention.

According to a first aspect of the invention there is provided a nucleic acid molecule encoding a polypeptide which is critical for survival and growth of the yeast *Candida albicans* and which nucleic acid molecule comprises any of the sequences of nucleotides illustrated in any of Sequence ID Nos. 1 to 9.

Whilst the molecules defined herein have been established as being critical for growth and metabolism of *Candida albicans*, for some of the molecules no apparent functionality has been assigned by virtue of the fact that no functionally related sequences in other prokaryotic or eukaryotic organism can be found in respective databases. Thus, advantageously these sequences may be species specific in which case they may be used be used as selective targets for treatment of diseases mediated by *Candida Albicans* infection. Thus, in one aspect of the invention the nucleic acid molecules preferably comprise the sequences identified in sequence ID Nos. 1, 4, 5 to 9.

In another aspect of the invention the sequences have been arranged functionally and of nucleotides illustrated in Sequence ID Nos. 2 or 3 are preferred and even more preferably in Sequence ID No. 2 and fragments or derivatives of said nucleic acid molecules.

Letters utilised in the sequences according to the invention which are not recognisable as letters of the genetic code signify a position in the nucleic acid sequence where one or more of bases A, G, C or T can occupy the nucleotide position. Representative letters used to identify the range of bases which can be used are as follows:

M: A or C
R: A or G
W: A or T
S: C or G
Y: C or T
K: G or T
V: A or C or G
H: A or C or T
D: A or C or T
B: C or G or T
N: G or A or T or C

In one embodiment of each of the above-identified aspects of the invention the nucleic acid may comprise a mRNA molecule or alternatively a DNA and preferably a cDNA molecule.

Also provided by the present invention is a nucleic acid molecule capable of hybridising to the nucleic acid molecules illustrated in any of FIGS. 1 to 9 under high stringency conditions such as antisense molecule and which conditions are generally known to those of skill in the art.

Stringency of hybridisation as used herein refers to conditions under which polynucleic acids are stable. The stability of hybrids is reflected in the melting temperature (Tm) of the hybrids. Tm can be approximated by the formula:

$$81.5° C.+16.6(Log_{10}[Na^+]+0.41(\% \text{ G\&C})-600 \text{ L/L}$$

wherein L is the length of the hybrids in nucleotides. Tm decreases approximately by 1–1.5° C. with every 1% decrease in sequence homology.

The term "stringency" refers to the hybridisation conditions wherein a single-stranded nucleic acid joins with a complementary strand when the purine or pyramidine bases therein pair with their corresponding base by hydrogen bonding. High stringency conditions favour homologous base pairing whereas low stringency conditions disfavour non-homologous base pairing.

"Low stringency" conditions comprise, for example, a temperature of about 37° C. or less, a formamide concentration of less than about 50%, and a moderate to low salt (SSC) concentration; or, alternatively, a temperature of about 50° C. or less, and a moderate to high salt (SSPE) concentration, for example 1M NaCl.

"High stringency" conditions comprise, for example, a temperature of about 42° C. or less, a formamide concentration of less than about 20%, and a low salt (SSC) concentration; or, alternatively, a temperature of about 65° C., or less, and a low salt (SSPE) concentration. For example, high stringency conditions comprise hybridization in 0.5 M NaHPO$_4$, 7% sodium dodecyl sulfate (SDS), 1 mM EDTA at 65° C. (Ausubel, F. M. et al. *Current Protocols in Molecular Biology*, Vol. I, 1989; Green Inc. New York, at 2.10.3).

"SSC" comprises a hybridization and wash solution. A stock 20× SSC solution contains 3M sodium chloride, 0.3M sodium citrate, pH 7.0.

"SSPE" comprises a hybridization and wash solution. A 1× SSPE solution contains 180 mM NaCl, 9 mM Na$_2$HPO$_4$ and 1 mM EDTA, pH 7.4.

The nucleic acid capable of hybridising to nucleic acid molecules according to the invention will generally be at least 70%, preferably at least 80 or 90% and more preferably at least 95% homologous to the nucleotide sequences illustrated in any of FIGS. 1 to 9.

The DNA molecules according to the invention may, advantageously, be included in a suitable expression vector to express polypeptides encoded therefrom in a suitable host which are critical for growth and survival of *Candida albicans*.

An expression vector according to the invention includes a vector having a nucleic acid according to the invention operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for expression of a polypeptide according to the invention. Thus, in a further aspect, the invention provides a process for preparing polypeptides according to the invention which comprises cultivating a host cell, transformed, transfected or infected with an expression vector as described above under conditions to provide for expression by the vector of a coding sequence encoding the polypeptides, and recovering the expressed polypeptides.

The vectors may be, for example, plasmid, virus or phage vectors provided with an origin of replication, optionally a promoter for the expression of said nucleotide and optionally a regulator of the promoter. The vectors may contain one or more selectable markers, such as, for example, ampicillin resistance.

Regulatory elements required for expression include promoter sequences to bind RNA polymerase and transcription initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art.

Polynucleotides according to the invention may be inserted into the vectors described in an antisense orientation in order to provide for the production of antisense RNA. Antisense RNA or other antisense nucleic acids may be produced by synthetic means.

In accordance with the present invention, a defined nucleic acid includes not only the identical nucleic acid but also any minor base variations including in particular, substitutions in bases which result in a synonymous codon (a different codon specifying the same amino acid residue) due to the degenerate code. The term "nucleic acid sequence" also includes the complementary sequence to any single stranded sequence given regarding base variations.

The present invention also comprises within its scope proteins or polypeptides expressed by the nucleic acid molecules according to the invention or a functional equivalent, derivative or bioprecursor thereof.

The present invention also advantageously provides nucleic acid sequences of at least approximately 10 contiguous nucleotides of a nucleic acid according to the invention and preferably from 10 to approximately 120 nucleotides. In another aspect of the invention, nucleotide acid sequences are provided from 10 to 50 nucleotides. These sequences may, advantageously be used as probes or primers to initiate replication, or the like. Such nucleic acid sequences may be produced according to techniques well known in the art, such as by recombinant or synthetic means. They may also be used in diagnostic kits or the like for detecting the presence of a nucleic acid according to the invention. These tests generally comprise contacting the probe with the sample under hybridising conditions and detecting for the presence of any duplex or triplex formation between the probe and any nucleic acid in the sample.

According to the present invention, these probes may be anchored to a solid support. Preferably, they are present on an array so that multiple probes can simultaneously hybridise to a single biological sample. The probes can be spotted onto the array or synthesized in situ on the array. See Lockhart et al., Nature Biotechnology, Vol. 14, December 1996, "Expression monitoring by hybridization to high-density oligonucleotide arrays". A single array can contain more than up to more than a million different probes in discrete locations.

Advantageously, the nucleic acid sequences, according to the invention may be produced using such recombinant or synthetic means, such as for example using PCR cloning mechanisms which generally involve making a pair of primers, which may be between approximately 10 to 120 nucleotides to a region of the gene which is desired to be cloned, bringing the primers into contact with mRNA, cDNA, or genomic DNA from a cell, performing a polymerase chain reaction under conditions which bring about amplification of the desired region, isolating the amplified region or fragment and recovering the amplified DNA. Generally, such techniques as defined herein are well known in the art, such as described in Sambrook et al (Molecular Cloning: a Laboratory Manual, 1989).

The nucleic acids or oligonucleotides according to the invention may carry a revealing label. Suitable labels include radioisotopes such as $^{32}$p or $^{39}$S, enzyme labels or other protein labels such as biotin or fluorescent markers. Such labels may be added to the nucleic acids or oligonucleotides of the invention and may be detected using known techniques per se.

The polypeptide or protein according to the invention includes all possible amino acid variants encoded by the nucleic acid molecule according to the invention including a polypeptide encoded by said molecule and having conservative amino acid changes. Polypeptides according to the invention further include variants of such sequences, including naturally occurring allelic variants which are substantially homologous to said polypeptides. In this context, substantial homology is regarded as a sequence which has at least 70%, preferably 80 or 90% amino acid homology with the polypeptides encoded by the nucleic acid molecules according to the invention.

Nucleic acids and polypeptides which are particularly preferred are those comprising the sequences of nucleotides provided in SEQ ID NOS: 1–3 and polypeptides provided in SEQ ID NOS: 10–12. However, a particularly preferred nucleic acid comprises the sequences of nucleotides provided as SEQ ID NOS: 2 and/or 3, and their corresponding amino acid sequences identified as SEQ ID NOS: 11 and 12.

With reference to the nucleic acids of this invention and the protein encoded thereby, amino acid sequence SEQ ID NO: 10 is the translation of SEQ ID NO:1; SEQ ID NO:1 is the translation of SEQ ID NO:2; SEQ ID NO:12 is the translation of SEQ ID NO:3; SEQ ID NO: 16 is the translation of SEQ ID NO:4; SEQ ID NO:13 is the translation of SEQ ID NO:5; SEQ ID NO:14 is the translation of SEQ ID NO:6 and SEQ ID NO:15 is the translation of SEQ ID NO:7.

Nucleotide sequences according to the invention are particularly advantageous as selective therapeutic targets for treating *Candida albicans* associated infections. For example, an antisense nucleic acid capable of binding to the nucleic acid sequence illustrated in any of SEQ ID NOS: 1–9 may be used to selectively inhibit expression of the corresponding polypeptides, leading to impaired growth of the *Candida albicans* with reductions of associated illnesses or diseases (see FIG. 5).

The nucleic acid molecule or the polypeptide according to the invention may be used as a medicament, or in the preparation of a medicament, for treating diseases or conditions associated with *Candida albicans* infection.

Advantageously, the nucleic acid molecule or the polypeptide according to the invention may be provided in a pharmaceutical composition together with a pharmaceutically acceptable carrier, diluent or excipient therefor.

The present invention is further directed to inhibiting expression of nucleic acids according to the invention in vivo by the use of antisense technology. Antisense technology can be used to control gene expression through triple-helix formation of antisense DNA or RNA, both of which methods are based on binding of a polynucleotide to DNA or RNA. For example, the 5' coding portion or the mature protein sequence, which encodes for the protein of the present invention, is used to design an antisense RNA oligonucleotide of from 10 to 50 base pairs in length. A DNA oligonucleotide is designed to be complementary to a region of the gene involved in transcription (triple-helix—see Lee et al. Nucl. Acids Res., 6:3073 (1979); Cooney et al., Science, 241:456 (1988); and Dervan et al., Science, 251: 1360 (1991), thereby preventing transcription and the production of the corresponding protein. The antisense RNA oligonucleotide hybridises to the mRNA in vivo and blocks translation of an mRNA molecule into the corresponding protein (antisense—Okano, J. Neurochem., 56:560 (1991); Oligodeoxynucleotides as Antisense Inhibitors of Gene Expression, CRC Press, Boca Raton, Fla. (1988)).

Antibodies to the protein or polypeptide of the present invention may, advantageously, be prepared by techniques which are known in the art. For example, polyclonal antibodies may be prepared by inoculating a host animal, such as a mouse, with the polypeptide according to the invention or an epitope thereof and recovering immune serum. Monoclonal antibodies may be prepared according to known techniques such as described by Kohler R. and Milstein C., Nature (1975) 256, 495–497.

Antibodies according to the invention may also be used in a method of detecting for the presence of a polypeptide according to the invention, which method comprises reacting the antibody with a sample and identifying any protein bound to said antibody. A kit may also be provided for performing said method which comprises an antibody according to the invention and means for reacting the antibody with said sample.

Proteins which interact with the polypeptide of the invention may be identified by investigating protein—protein interactions using the two-hybrid vector system first proposed by Chien et al. (1991).

This technique is based on functional reconstitution in vivo of a transcription factor which activates a reporter gene. More particularly the technique comprises providing an appropriate host cell with a DNA construct comprising a reporter gene under the control of a promoter regulated by a transcription factor having a DNA binding domain and an activating domain, expressing in the host cell a first hybrid DNA sequence encoding a first fusion of a fragment or all of a nucleic acid sequence according to the invention and either said DNA binding domain or said activating domain of the transcription factor, expressing in the host at least one second hybrid DNA sequence, such as a library or the like, encoding putative binding proteins to be investigated together with the DNA binding or activating domain of the transcription factor which is not incorporated in the first fusion; detecting any binding of the proteins to be investigated with a protein according to the invention by detecting for the presence of any reporter gene product in the host cell; optionally isolating second hybrid DNA sequences encoding the binding protein.

An example of such a technique utilises the GAL4 protein in yeast. GAL4 is a transcriptional activator of galactose metabolism in yeast and has a separate domain for binding to activators upstream of the galactose metabolising genes as well as a protein binding domain. Nucleotide vectors may be constructed, one of which comprises the nucleotide residues encoding the DNA binding domain of GAL4. These binding domain residues may be fused to a known protein encoding sequence, such as for example the nucleic acids according to the invention. The other vector comprises the residues encoding the protein binding domain of GAL4. These residues are fused to residues encoding a test protein. Any interaction between polypeptides encoded by the nucleic acid according to the invention and the protein to be tested leads to transcriptional activation of a reporter molecule in a GAL4 transcription deficient yeast cell into which the vectors have been transformed. Preferably, a reporter molecule such as β-galactosidase is activated upon restoration of transcription of the yeast galactose metabolism genes.

Further provided by the present invention is one or more *Candida albicans* cells comprising an induced mutation in the DNA sequence encoding the polypeptide according to the invention.

A further aspect of the invention provides a method of identifying compounds which selectively inhibit or interfere with the expression, the functionality of polypeptides expressed from the nucleotides sequences illustrated in any of SEQ ID NOS: 1–9, or the metabolic pathways in which these polypeptides are involved and which are critical for growth and survival of *Candida albicans*, which method comprises (a) contacting a compound to be tested with one or more *Candida albicans* cells having a mutation in a nucleic acid molecule according to the invention which mutation results in overexpression or underexpression of said polypeptides in addition to one or more wild type *Candida* cells, (b) monitoring the growth and/or activity of said mutated cell compared to said wild type wherein differential growth or activity of said one or more mutated *Candida* cells provides an indication of selective action of said compound on said polypeptide or another polypeptide in the same or a parallel pathway.

Compounds identifiable or identified using the method according to the invention, may advantageously be used as a medicament, or in the preparation of a medicament to treat diseases or conditions associated with *Candida albicans* infection. These compounds may also advantageously be included in a pharmaceutical composition together with a pharmaceutically acceptable carrier, diluent or excipient therefor.

A further aspect of the invention provides a method of identifying DNA sequences from a cell or organism which DNA encodes polypeptides which are critical for growth or survival, which method comprises (a) preparing a cDNA or genomic library from said cell or organism in a suitable expression vector which vector is such that it can either integrate into the genome in said cell or that it permits transcription of antisense RNA from the nucleotide sequences in said cDNA or genomic library, (b) selecting transformants exhibiting impaired growth and determining the nucleotide sequence of the cDNA or genomic sequence from the library included in the vector from said transformant. Preferably, the cell or organism may be any yeast or filamentous fungus, such as, for example, *Saccharomyces cerevisiae, Schizosaccharomyces pombe* or *Candida albicans*.

A further aspect of the invention provides a pharmaceutical composition comprising any of a compound, an antisense molecule or an antibody according to the invention together with a pharmaceutically acceptable carrier, diluent or excipient therefor.

The antisense molecules or indeed the compounds identified as agonists or antagonists of the nucleic acids or polypeptides according to the invention may be used in the form of a pharmaceutical composition, which may be prepared according to procedures well known in the art. Preferred compositions include a pharmaceutically acceptable vehicle or diluent or excipient, such as for example, a physiological saline solution. Other pharmaceutically acceptable carriers including other non-toxic salts, sterile water or the like may also be used. A suitable buffer may also be present allowing the compositions to be lyophilized and stored in sterile conditions prior to reconstitution by the addition of sterile water for subsequent administration. Incorporation of the polypeptides of the invention into a solid or semi-solid biologically compatible matrix may be carried out which can be implanted into tissues requiring treatment.

The carrier can also contain other pharmaceutically acceptable excipients for modifying other conditions such as pH, osmolarity, viscosity, sterility, lipophilicity, solubility or the like. Pharmaceutically acceptable excipients which permit sustained or delayed release following administration may also be included.

The polypeptides, the nucleic acid molecules or compounds according to the invention may be administered orally. In this embodiment they may be encapsulated and combined with suitable carriers in solid dosage forms which would be well known to those skilled in the art.

As would be well known to those of skill in the art, the specific dosage regime may be calculated according to the body surface area of the patient or the volume of body space to be occupied, dependent upon the particular route of administration to be used. The amount of the composition actually administered will, however, be determined by a medical practitioner, based on the circumstances pertaining to the disorder to be treated, such as the severity of the symptoms, the composition to be administered, the age, weight, and response of the individual patient and the chosen route of administration.

EXAMPLE 1

Identification of Novel Drug Targets in *C. Albicans* by Anti-Sense and Disruptive Integration The principle of the approach is based on the fact that when a particular *C. albicans* mRNA is inhibited by producing the complementary anti-sense RNA, the corresponding protein will decrease. If this protein is critical for growth or survival, the cell producing the anti-sense RNA will grow more slowly or will die.

Since anti-sense inhibition occurs at mRNA level, the gene copy number is irrelevant, thus allowing applications of the strategy even in diploid organisms.

Anti-sense RNA is endogenously produced from an integrative or episomal plasmid with an inducible promoter; induction of the promoter leads to the production of an RNA encoded by the insert of the plasmid. This insert will differ from one plasmid to another in the library. The inserts will be derived from genomic DNA fragments or from cDNA to cover—to the extent possible—the entire genome.

The vector is a proprietary vector allowing integration by homologous recombination at either the homologous insert or promoter sequence in the *Candida* genome. After introducing plasmids from cDNA or genomic libraries into *C. albicans*, transformants are screened for impaired growth after promoter (& thus anti-sense) induction in the presence of lithium acetate. Lithium acetate prolongs the G1 phase and thus allows anti-sense to act during a prolonged period of time during the cell cycle. Transformants which show impaired growth in both induced and non-induced media, thus showing a growth defect due to integrative disruption, are selected as well.

Transformants showing impaired growth are supposed to contain plasmids which produce anti-sense RNA to mRNAs critical for growth or survival. Growth is monitored by measuring growth-curves over a period of time in a device (Bioscreen Analyzer, Labsystems) which allows simultaneous measurement of growth-curves of 200 transformants.

Subsequently plasmids can be recovered from the transformants and the sequence of their inserts determined, thus revealing which mRNA they inhibit. In order to be able to recover the genomic or cDNA insert which has integrated into the *Candida* genome, genomic DNA is isolated, cut with an enzyme which cuts only once into the library vector (and estimated approx. every 4096 bp in the genome) and religated. PCR with primers flanking the insert will yield (partial) genomic or cDNA inserts as PCR fragments which can directly be sequenced. This PCR analysis (on ligation reaction) will also show us how many integrations occurred. Alternatively the ligation reaction is transformed to *E. coli* and PCR analysis is performed on colonies or on plasmid DNA derived thereof.

This method is employed for a genome-wide search for novel *C. albicans* genes which are important for growth or survival.

Materials & Methods

Construction of pGal1PNiST-1 (SEQ ID NO:21)

The backbone of the pGAL1PNiST-1 vector (integrative anti-sense SfiI-NotI vector) is pGEM11Zf(+) (Promega Inc.). First, the CaMAL2 EcoRI/SalI promoter fragment from pDBV50 (D. H. Brown et al. 1996) was ligated into EcoRI/SalI-opened pGEM11Zf(+) resulting in the intermediate construct pGEMMAL2P-1. Into the latter (MscI/CIP) the CaURA3 selection marker was cloned as a Eco47III/XmnI fragment derived from pRM2. The resulting pGEMMAL2P-2 vector was NotI/HindIII opened in order to accept the NotI-stuffer-SfiI cassette from pPCK1NiSCYCT-1 (EagI/HindIII fragment): pMAL2PNiST-1. Finally, the plasmid pGAL1PNiST-1 was constructed by exchanging the SalI/Ecl136II MAL2 promoter in pMAL2PNiST-1 by the XhoI/SmaI GAL1 promoter fragment derived from pRM2GAL1P.

Construction of pGal1PSiST-1 (SEQ ID ON:22)

The vector pGAL1PSiST-1 was created for cloning the small genomic DNA fragments (flanked by SfiI sites) behind the GAL1 promoter. The only difference with pGAL1PNiST-1 is that the hIFNβ (stuffer fragment) insert fragment in pGAL1PSiST-1 is flanked by two SfiI sites in stead of a SfiI and a NotI site as in pGAL1PNiST-1. To construct pGAL1PSiST-1 the EcoRI-HindIII fragment, containing hIFNβ flanked by a SfiI and a NotI site, of pMAL2pHiET-3 (unpublished) was exchanged by the EcoRI-HindIII fragment, containing hIFNβ flanked by two SfiI sites, from YCp50S-S (an *E. coli/S. cerevisiae* shuttle vector derived from the plasmid YCp50, which is deposited in the ATCC collection (number 37419; Thrash et al., 1985); an EcoRI-HindIII fragment, containing the gene hIFNβ, which is flanked by two SfiI sites, was inserted in YCp50, creating YCp50S-S), resulting into plasmid pMAL2PSiST-1. The MAL2 promoter from pMAL2PSiST-1 (by a NaeI-ball digest) was further replaced by the GAL1 promoter from pGAL1PNiST-1 (via a XhoI-FSPI digest), creating the vector pGAL1PSiST-1.

*Candida albicans* Genomic Library

Preparation of the Genomic DNA Fragments

A *Candida albicans* genomic DNA library with small DNA fragments (400 to 1,000 bp) was prepared. Genomic DNA of *Candida albicans* B2630 was isolated following a modified protocol of Blin and Stafford (1976). The quality of the isolated genomic DNA was checked by gel electrophoresis. Undigested DNA was located on the gel above the marker band of 26,282 bp. A little smear, caused by fragmentation of the DNA, was present. To obtain enrichment for genomic DNA fragments of the desired size, the genomic DNA was partially digested. Several restriction enzymes (AluI, HaeIII and RsaI; all creating blunt ends) were tried out. The appropriate digest conditions have been determined by titration of the enzyme. Enrichment of small DNA fragments was obtained with 70 units of AluI on 10 □g of genomic DNA for 20 min. T4 DNA polymerase (Boehringer) and dNTPs (Boehringer) were added to polish the DNA ends. After extraction with phenol-chloroform the digest was size-fractionated on an agarose gel. The genomic DNA fragments with a length of 500 to 1,250 bp were eluted from the gel by centrifugal filtration (Zhu et al., 1985). SfiI adaptors (5' GTTGGCCTTTT SEQ ID NO: 23) or (5' AGGCCAAC SEQ ID NO: 24) were attached to the DNA ends (blunt) to facilitate cloning of the fragments into the vector. Therefore, a 8-mer and 11-mer oligonucleotide (comprising the SfiI site) were kinased and annealed. After ligation of these adaptors to the DNA fragments a second size-fractionation was performed on an agarose gel. The DNA fragments of 400 to 1150 bp were eluted from the gel by centrifugal filtration.

Preparation of the pGAL1PSiST-1 Vector Fragment

The small genomic DNA fragments were cloned after the GAL1 promoter in the vector pGAL1PSIST-1. Qiagen-purified pGAL1PSIST-1 plasmid DNA was digested with SfiI and the largest vector fragment eluted from the gel by centrifugal filtration (Zhu et al., 1985). Ligation with a control DNA fragment, flanked by SfiI sites, was performed as a control. The ligation mix was electroporated to MC1061 *E. coli* cells. Plasmid DNA of 24 clones was analyzed. In all cases the control fragment was inserted in the pGAL1PSiST-1 vector fragment.

Upscaling

All genomic DNA fragments (450 ng) were ligated into the pGAL1PSiST-1 vector (20 ng). After electroporation at 2500V, 40 μF circa 400,000 clones were obtained. These clones were pooled into three groups and stored as glycerol slants. Also Qiagen-purified DNA was prepared from these clones. A clone analysis showed an average insert length of 600 bp and a percentage of 91 for clones with an insert. The size of the library corresponds to 5 times the diploid genome. The genomic DNA inserts are sense or anti-sense orientated in the vector.

*Candida albicans* cDNA Library

Total RNA was extracted from *Candida albicans* B2630 grown on respectively minimal (SD) and rich (YPD) medium as described by Chirgwin et al. in Sambrook et al 1996. mRNA was prepared from total RNA using the Invitrogen Fast Track procedure.

First strand cDNA is synthesised with the Superscript Reverse Transcriptase (BRL) and with an oligo dT-NotI Primer adapter. After second strand synthesis, cDNA is polished with Klenow enzyme and purified over a Sephacryl S-400 spun column. Phosphorylated SfiI adapters are then ligated to the cDNA, followed by digestion with the NotI restriction enzyme. The SfiI/NotI cDNA is then purified and sized on a Biogel column A150M.

First fraction contains approximately 38,720 clones by transformation, the second fraction only 1540 clones. Clone analysis:

Fr. I: 22/24 inserts, 16; 1000 bp, 4; 2000 bp, average size: 1500 bp.

Fr. II: 9/12 inserts, 3; 1000 bp, average size: 960 bp cDNA was ligated in a NotI/SfiI opened pGAL1PNiST-1 vector (anti-sense)

*Candida* Transformation

The host strain used for transformation is a *C. albicans* ura3 mutant, CAI-4, which contains a deletion in orotidine-5=-phosphate decarboxylase and was obtained from William Fonzi, Georgetown University (Fonzi and Irwin). CAI-4 was transformed with the above described cDNA library or genomic library using the *Pichia* spheroplast module (Invitrogen). Resulting transformants were plated on minimal medium supplemented with glucose (SD, 0.67% or 1.34% Yeast Nitrogen base w/o amino acids+2% glucose) plates and incubated for 2–3 days at 30° C.

Screening for Mutants

Starter cultures were set up by inoculating each colony in 1 ml SD medium and incubating overnight at 30° C. and 300 rpm. Cell densities were determined using a Coulter counter (Coulter Z1; Coulter electronics limited). 250.000 cells/ml were inoculated in 1 ml SD medium and cultures were incubated for 24 hours at 30° C. and 300 rpm. Cultures were washed in minimal medium without glucose (S) and the pellet resuspended in 650 µl S medium. 8 µl of this culture is used for inoculating 400 µl cultures in a Honeywell-100 plate (Bioscreen analyzer; Labsystems). Each transformant was grown during three days in S medium containing LiAc; pH 6.0, with 2% glucose/2% maltose or 2% galactose/2% maltose respectively while shaking every 3 minutes for 20 seconds. Optical densities were measured every hour during three consecutive days and growth curves were generated (Bioscreen analyzer; Labsystems).

Growth curves of transformants grown in respectively anti-sense non-inducing (glucose/maltose) and inducing (galactose/maltose) medium are compared and those transformants showing impaired growth upon anti-sense induction are selected for further analysis. Transformants showing impaired growth by virtue of integration into a critical gene are also selected.

Isolation of Genomic or cDNA Inserts

Putatively interesting transformants are grown in 1.5 ml SD overnight and genomic DNA is isolated using the Nucleon MI Yeast kit (Clontech). Concentration of genomic DNA is estimated by analyzing a sample on an agarose gel.

20 ng of genomic DNA is digested for three hours with an enzyme that cuts uniquely in the library vector (SacI for the genomic library; PstI for the cDNA library) and treated with RNAse. Samples are phenol/chloroform extracted and precipitated using NaOAc/ethanol.

The resulting pellet is resuspended in 500 µl ligation mixture (1× ligation buffer and 4 units of T4 DNA ligase; both from Boehringer) and incubated overnight at 16° C.

After denaturation (20 min 65° C.), purification (phenol/chloroform extraction) and precipitation (NaOAc/ethanol) the pellet is resuspended in 10 µl MilliQ (Millipore) water.

PCR Analysis

Inverse PCR is performed on 1 µl of the precipitated ligation reaction using library vector specific primers (oligo23 5' TGC-AGC-TCG-ACC-TCG-ACT-G 3' SEQ ID NO: 17 and oligo25 5' GCG-TGA-ATG-TAA-GCG-TGA-C 3' SEQ ID NO: 18 for the genomic library; 3pGALNistPCR primer: 5'TGAGCAGCTCGCCGTCGCGC 3' SEQ ID NO: 19 and 5pGALNistPCR primer: 5'GAGTTATACCCTG-CAGCTCGAC 3' SEQ ID NO: 20 for the cDNA library; both from Eurogentec) for 30 cycles each consisting of (a) 1 min at 95° C., (b) 1 min at 57° C., and (c) 3 min at 72° C. In the reaction mixture 2.5 units of Taq polymerase (Boehringer) with TaqStart antibody (Clontech) (1:1) were used, and the final concentrations were 0.2 µM of each primer, 3 mM $MgCl_2$ (Perkin Elmer Cetus) and 200 µM dNTPs (Perkin Elmer Cetus). PCR was performed in a Robocycler (Stratagene).

Sequence Determination

Resulting PCR products were purified using PCR purification kit (Qiagen) and were quantified by comparison of band intensity on EtBr stained agarose gel with the intensity of DNA marker bands. The amount of PCR product (expressed in ng) used in the sequencing reaction is calculated as the length of the PCR product in basepairs divided by 10. Sequencing reactions were performed using the ABI Prism BigDye Terminator Cycle Sequencing Ready Reaction Kit according to the instructions of the manufacturer (PE Applied Biosystems, Foster City, Calif.) except for the following modifications.

The total reaction volume was reduced to 15 µl. Reaction volume of individual reagents were changed accordingly. 6.0 µl Terminator Ready Reaction Mix was replaced by a mixture of 3.0 µl Terminator Ready Reaction Mix+3.0 µl Half Term (GENPAK Limited, Brighton, UK). After cycle sequencing, reaction mixtures were purified over Sephadex G50 columns prepared on Multiscreen HV opaque microtiter plates (Millipore, Molsheim, Fr) and were dried in a speedVac. Reaction products were resuspended in 3 µl loading buffer. Following denaturation for 2 min at 95° C., 1 µl of sample was applied on a 5% Long Ranger Gel (36 cm well-to-read) prepared from Singel Packs according to the supplier's instructions (FMC BioProducts, Rockland, Me.). Samples were run for 7 hours 2× run on a ABI 377XL DNA sequencer. Data collection version 2.0 and Sequence analysis version 3.0 (for basecalling) software packages are from PE Applied Biosystems. Resulting sequence text files were copied onto a server for further analysis.

Sequence Analysis

Nucleotide sequences were imported in the VectorNTI software package (InforMax Inc, North Bethesda, Md., USA), and the vector and insert regions of the sequences were identified. Sequence similarity searches against public and commercial sequence databases were performed with the BLAST software package (Altschul et al., 1990) version 1.4. Both the original nucleotide sequence and the six-frame conceptual translations of the insert region were used as query sequences. The used public databases were the EMBL nucleotide sequence database (Stoesser et al., 1998), the SWISS-PROT protein sequence database and its supplement TrEMBL (Bairoch and Apweiler, 1998), and the ALCES *Candida albicans* sequence database (Stanford University, University of Minnesota). The commercial sequence databases used were the LifeSeq® human and PathoSeq® microbial genomic databases (Incyte Pharmaceuticals Inc., Palo Alto, Calif., USA), and the GENESEQ patent sequence database (Derwent, London, UK). Three major results were obtained on the basis of the sequence similarity searches: function, novelty, and specificity. A putative function was deduced on the basis of the similarity with sequences with a known function, the novelty was based on the absence or presence of the sequences in public databases, and the specificity was based on the similarity with vertebrate homologues.

Methods

Blastx of the nucleic acid sequences against the appropriate protein databases: Swiss-Prot for clones of which the complete sequence is present in the public domain, and paorfp (PathoSeq™) for clones of which the complete sequences is not present in the public domain.

The protein to which the translated nucleic acid sequence corresponds to is used as a starting point. The differences between this protein and our translated nucleic acid sequences are marked with a double line and annotated above the protein sequence.

The following symbols are used:

A one-letter amino acid code or the ambiguity code X is used if our translated nucleic acid sequence has another amino acid on a certain position, The stop codon sign * is used if our translated nucleic acid sequence has a stop codon on a certain position, The letters fs (frame shift) are used if a frame shift occurs in our translated nucleic acid sequence, and another reading frame is used, The words ambiguity or ambiguities are used if a part of our translated nucleic acid sequence is present in the proteins, but not visible in the alignments of the blast results, The phrase "missing sequence" is used if the translated nucleic acid sequence does not comprise that part of the protein.

Blastx: compares the six-frame conceptual translation products of a nucleotide query sequence (both strands) against a protein sequence database.

Antisense Experiments

Clones 383c_cp, 392c_cp, 417c_cpG2L, 325c_af, 322c_cp, 26g3, and 409c_cp were transformed with plasmid pGAL1PSiST-1 containing the galactose inducible promotor/expression cassette. The plasmid was modified to include antisense molecules capable of binding to RNA expressed from DNA corresponding to SEQ ID NOs: 1–2 and SEQ ID NOs 4–8 natively present the *Candida albicans* cell. Following transformation the cells were grown in the presence of glucose or galactose to determine the effect of the induced antisense molecule on protein expression and on *Candida albicans* cell growth. An exemplary growth curve is provided in FIG. 5. All cells transformed with the antisense molecules demonstrated significant growth reduction.

Gene Knock-Outs

Figure 4:
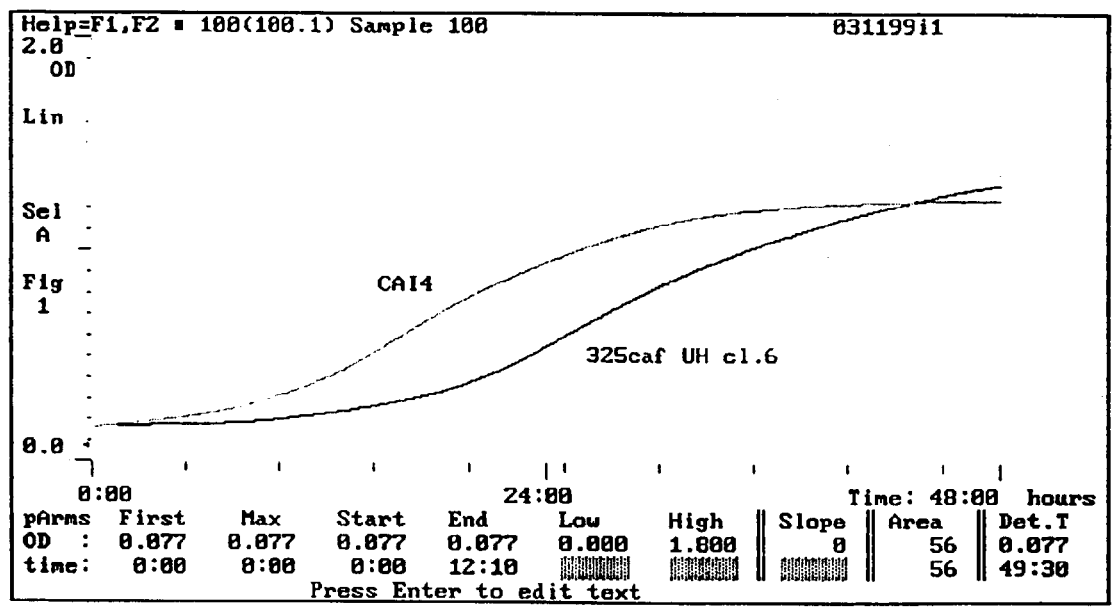
FIG. 4 is a representative growth curve of a *Candida albicans* knock out strain as compared to wild type *Candida albicans*.

To verify that the growth effect was due to the interference with the identified gene and to support the specificity of the antisense effect, single and double allele knock-outs were made in the identified genes using the URA-blaster method (Fonzi and Irwin 1993). FIG. 4 provides an example of a growth curve for a double allele knock-out as compared to the wild-type strain CAI4. Growth curves are shown as the measurement of optical density (Y-axis) over time in hours (X-axis). The optical density is a measure for the number of cells present and this a measure for growth. A reduction in growth was observed for this double knock-out as compared to the wild-type strain.

Screening for Compounds Modulating Expression of Polypeptides critical for growth and survival of *C. albicans*

The method proposed is based on observations (Sandbaken et al., 1990; Hinnebusch and Liebman 1991; Ribogene PCT WO 95/11969, 1995) suggesting that underexpression or overexpression of any component of a process (e.g. translation) could lead to altered sensitivity to an inhibitor of a relevant step in that process. Such an inhibitor should be more potent against a cell limited by a deficiency in the macromolecule catalyzing that step and/or less potent against a cell containing an excess of that macromolecule, as compared to the wild type (WT) cell.

Mutant yeast strains, for example, have shown that some steps of translation are sensitive to the stoichiometry of macromolecules involved. (Sandbaken et al. 1996). Such strains are more sensitive to compounds, which specifically perturb translation (by acting on a component that participates in translation) but are equally sensitive to compounds with other mechanisms of action.

This method thus not only provides a means to identify whether a test compound perturbs a certain process but also an indication of the site at which it exerts its effect. The component which is present in altered form or amount in a cell whose growth is affected by a test compound is potentially the site of action of the test compound.

The assay involves measurement of growth of an isogenic strain which has been modified only in a certain specific allele, relative to a wild type (WT) *C. albicans* strain, in the presence of R-compounds. Strains can be ones in which the expression of a specific essential protein is impaired upon induction of anti-sense or strains which carry disruptions in an essential gene. An in silico approach to finding novel essential genes in *C. albicans* will be performed. A number of essential genes identified in this way will be disrupted (in one allele) and the resulting strains can be used for comparative growth screening.

Assay for High Throughput Screening for Drugs

35 µl minimal medium (S medium+2% galactose+2% maltose) is transferred in a transparent flat-bottomed 96 well plate using an automated pipetting system (Multidrop, Labsystems). A 96-channel pipettor (Hydra, Robbins Scientific) transfers 2.5 µl of R-compound at $10^{-3}$ M in DMSO from a stock plate into the assay plate.

The selected *C. albicans* strains (mutant and parent (CAI-4) strain) are stored as glycerol stocks (15%) at −70° C. The strains are streaked out on selective plates (SD medium) and incubated for two days at 30° C. For the parent strain, CAI-4, the medium is always supplemented with 20 µg/ml uridine. A single colony is scooped up and resuspended in 1 ml minimal medium (S medium+2% galactose+2% maltose). Cells are incubated at 30° C. for 8 hours while shaking at 250 rpm. A 10 ml culture is inoculated at 250,000 cells/ml. Cultures are incubated at 30° C. for 24 hours while shaking at 250 rpm. Cells are counted in Coulter counter and the final culture (S medium+2% galactose+2% maltose) is inoculated at 20,000 to 50,000 cells/ml. Cultures are grown at 30° C. while shaking at 250 rpm until a final OD of 0.24 (+/−0.04) 600 nM is reached.

200 µl of this yeast suspension is added to all wells of MW96 plates containing R-compounds in a 450 (or 250) µl total volume. MW96 plates are incubated (static) at 30° C. for 48 hours.

Optical densities are measured after 48 hours.

Test growth is expressed as a percentage of positive control growth for both mutant (x) and wild type (y) strains. The ratio (x/y) of these derived variables is calculated.

REFERENCES

Altschul, S. F., W. Gish, W. Miller, E. W. Myers, and D. J. Lipman, 1990, Basic Local Alignment Search Tool, J. Mol. Biol. 215: 403–410.

Thrash C., Bankier A. T., Barrell B. G. and Sternglanz R. (1985) *Proc. Natl. Acad. Sci.* USA 82: 4374–4378.

Blin N. and Stafford D. W. (1976) *Nucleic Acids Res.* 3: 2303–2308.

Zhu J., Kempenaers W., Van Der Straeten D., Contreras R., and Fiers W. (1985) *Bio/Technology* 3: 1014–1016.

Sambrook J., Fritsch E. F. and Maniatis T. (1989) Molecular Cloning: A Laboratory Manual, 2nd Ed., Cold Spring Harbor Laboratory, Cold Spring Harbor, N.Y.

Fonzi W. and Irwin H. (1993) *Genetics* 134:717–728.

Altschul S. F, Gish W., Miller W., Myers E. W., Lipman D. J. (1990) *J. Mol. Biol.* 215(3):403–410.

Bairoch A. and Apweiler R. (1998) *Nucleic Acids Res.* 26(1):38–42.

Stoesser G., Moseley M. A., Sleep J., McGowran M., Garcia-Pastor M., Sterk P. (1998) *Nucleic Acids Res.* 26(1):8–15.

Chien et al., (1991) Proc. Natl. Acad. Sci USA 88, 9578–9582.

Sandbaken M. G. Lupisella J. A., DiDomenico B. and Chakraburtty K., *J. Biol. Chem.* 265:15838–15844, 1990.

Hinnebusch A. G. and Liebman S. W., in: The Molecular Biology of the Yeast *Saccharomyces*, Broach J. R., Pringle J. R. and Jones E. W., eds., CSH Laboratory Press; NY 1991.

Patent application RiboGene Inc., PCT WO 95./11969, 1995.

Brown, D. H. et al., Molecular General Genetics 251 (1) 75–80, 1996.

Altschul, S. F., W. Gish, W. Miller, E. W. Myers, and D. J. Lipman. 1990. Basic local alignment search tool. J. Mol. Biol. 215: 403–410.

Arndt, G. M., D. Atkins, M. Patrikakis, and J. G. Izant 1995. Gene regulation by antisense RNA in the fission yeast *Schizosaccharomyces pombe*. Mol. Gen. Genet. 248:293–300.

Atkins, D., and W. L. Gerlach. 1994. Artificial ribozyme and antisense gene expression in *S. cerevisiae*. Antisense research and development 4:109–117.

Atkins, D., G. M. Arndt, and J. G. Izant 1994. Antisense gene expression in yeast. Biol. Chem. Hoppe-Seyler. 375:721–729.

Atkins, D., M. Patrikakis, J. G. Izant 1995. The ade6 gene of the fission yeast as a target for antisense and ribozyme RNA-mediated suppression. Antisense Research & Development. 5(4):295–305.

Bairoch, A., and R. Apweiler. 1998. The SWISS-PROT protein sequence data bank and its supplement TrEMBL in 1998. Nucleic Acids Res. 26: 38–42. Baudin, A., O. Ozier-Kalogeropoulos, A. Denouel, F. Lacroute, C. Cullin. 1993. A simple and efficient method for direct gene deletion in *Saccharomyces cerevisiae*. Nucleic Acids Research. 21(14):3329–30.

Blin, N., and D. W. Stafford. 1976. Nucleic Acids Res. 3: 2303–2308.

Dujon, B. 1998. European Functional Analysis Network (EUROFAN) and the functional analysis of the *Saccharomyces cerevisiae* genome. Electrophoresis. 19:617–624.

Del Rosario, M., J. C. Stephans, J. Zakel, J. Escobedo, and K. Giese. 1996. Positive selection system to screen for inhibitors of human immunodeficiency virus-1 transcription. Nature Biotechnology. 14:1592–1596.

Fairhead, C., A. Thierry, F. Denis, M. Eck, and B. Dujon. 1998. AMass-murder≃ of ORFs from three regions of chromosome XI from *Saccharomyces cerevisiae*. Gene. 223:33–46.

Ferbeyre, G., J. Bratty, H. Chen, R. Cedergren. 1996. Cell cycle arrest promotes trans-hammerhead ribozyme action in yeast. Journal of Biological Chemistry. 271(32):19318–23.

Fleischmann, R. D., M. D. Adams, O. White, R. A. Clayton, E. F. Kirkness, A. R. Kerlavage, C. J. Bult, J. F. Tomb, B. A. Dougherty, J. M. Merrick. 1995. Whole-genome random sequencing and assembly of *Haemophilus influenzae*. Science. 269: 496–512

Fonzi, W. A., and M. Y. Irwin. 1993. Isogenic strain construction and gene mapping in *Candida albicans*. Genetics 134:717–728.

Fraser, C. M., J. D. Gocayne, O. White, M. D. Adams, R. A. Clayton, R. D. Fleischmann, C. J. Bult, A. R. Kervalage, G. Sutton, J. M. Kelley. 1995. The minimal gene complement of *Mycoplasma genitalium*. Science 270:397–403.

Giese, K. 1997. Method and construct for screening for inhibitors of transcriptional activation. International patent application WO 97/10360.

Hahn, S. Guarente L. 1988. Yeast HAP2 and HAP3: transcriptional activators in a heteromeric complex. Science. 240(4850):317–21

Heid, C. A., J. Stevens, K. J. Livak, and P. M. Williams. 1996. Real time quantitative PCR. Genome Methods 6:986–994.

Jayaram, M., A. Sutton, J. R. Broach. 1985. Properties of REP3: a cis-acting locus required for stable propagation of the *Saccharomyces cerevisiae* plasmid 2 microns circle. Molecular & Cellular Biology. 5(9):2466–75.

Jeong, S. W., W. H. Lang, R. H. Reeder. 1996. The yeast transcription terminator for RNA polymerase I is designed to prevent polymerase slippage. Journal of Biological Chemistry. 271(27):16104–10.

Johnson, F. B., D. A. Sinclair, and L. Guarente. 1999. Molecular Biology of aging. Cell. 96:291–302.

Leuker, C. E., A. Sonneborn, S. Delbruck, J. F. Ernst. 1997. Sequence and promoter regulation of the PCK1 gene encoding phosphoenolpyruvate carboxykinase of the fungal pathogen *Candida albicans*. Gene. 192(2):235–40.

Lie, Y. S., and C. J. Petropoulos. 1998. Advances in quantitative PCR technology: 5' nuclease assays. Current Opinion in Biotechnology 9:43–48.

Livak, K. J., S. J. Flood, J. Marmaro, W. Giusti, K. Deetz. 1995. Oligonucleotides with fluorescent dyes at opposite ends provide a quenched probe system useful for detecting PCR product and nucleic acid hybridization. Genome Research. 4(6):357–62.

Mandart, E. 1998. Effects of mutations in the *Saccharomyces cerevisiae* RNA14 gene on the abundance and polyadenylation of its transcripts. Mol. Gen. Genet. 258:16–25.

McMahon, S. B., H. A. Van Buskirk, K. A. Dugan, T. D. Copeland, and M. D. Cole. 1998. The novel ATM-related protein TRRAP is an essential cofactor for the c-Myc and E2F oncoproteins. Cell. 94:363–74.

Murray, J. A. H., M. Scarpa, N. Rossi, G. Cesareni 1987. Antagonistic controls regulate copy number of the yeast 2μ plasmid. EMBO J. 6:4205–4212.

Nasr, F., A. Bécam, P. P. Slonimski, and C. J. Herbert. 1994. YBR1012, an essential gene from *S. cerevisiae*: construction of an RNA-antisense conditional allele and isolation of a multicopy suppressor. CR Acad. Sci. Paris. 317: 607–613

Nasr, F., A. Bécam, S. C. Brown, D. De Nay. P. P. Slonimski, and C. J. Herbert. 1995. Artificial antisense regulation of YBR1012 an essential gene from *S. cerevisiae* which is important for progression through G1/S. Mol. Gen. Genet. 249:51–57.

Nomura, T., N. Fujita, A. Ishihama. 1985. Promoter selectivity of *E. coli* RNA polymerase: analysis of the promoter system of convergently-transcribed dnaQ-rnh genes. Nucleic Acids Research. 13(21):7647–61.

Orlando, C., P. Pinzani, and M. Pazzagli. 1998. Developments in quantitative PCR. Clin. Chem. Lab. Med. 36(5): 255–269.

Pla, J., C. Gil, F. Monteoliva, M. Sanchez, and C. Nombela. 1996. Understanding *Candida albicans* at the molecular level. Yeast. 12:1677–1702.

Reeder, R. H. and W. H. Lang. 1997. Terminating transcription in eukaryotes: lessons learned from RNA polymerase I. Trends in Biochemical Sciences. 22(12):473–7, 1997

Sambrook, J., E. F. Fritsch, and T. Maniatis. 1989. Molecular Cloning: A Laboratory Manual, 2nd Ed., Cold Spring Harbor Laboratory, Cold Spring Harbor, N.Y.

Sinclair, D. A., L. Guarente. 1997. Extrachromosomal rDNA circles—a cause of aging in yeast. Cell. 91(7):1033–42.

Smith, V., D. Botstein, and P. O. Brown. 1995. Genetic footprinting: A genomic strategy for determining a gene=s function given its sequence. Proc. Natl. Acad. Sci. USA. 92:6479–6483.

Stoesser, G., Moseley M. A., Sleep J., McGowran M., Garcia-Pastor M., Sterk P. 1998. Nucleic Acids Res. 26(1):8–15.

Thompson-Jager, S. Domdey H. 1990. The intron of the yeast actin gene contains the promoter for an antisense RNA. Current Genetics. 17(3):269–73.

Thompson, J. R., E. Register, J. Curotto, M. Kurtz, and R. Kelly. 1998. An improved protocol for the preparation of yeast cells for transformation by electroporation. Yeast. 14:565–571.

Thrash, C., A. T. Bankier, B. G. Barrell, and R. Sternglanz. 1985. Proc. Natl. Acad. Sci. USA 82: 4374–4378.

Van Duin, M., J. van Den Tol, J. H. Hoeijmakers, D. Bootsma, I. P. Rupp, P. Reynolds, L. Prakash, and S. Prakash. 1989. Conserved pattern of antisense overlapping transcription in the homologous human ERCC-1 and yeast RAD10 DNA repair gene regions. Molecular & Cellular Biology. 9(4):1794–8.

Wach, A., A. Brachat, R. Pohlmann, P. Philippsen. 1994. New heterologous modules for classical or PCR-based gene disruptions in *Saccharomyces cerevisiae*. Yeast. 10(13):1793–808.

Wilson, R. B., D. Davis, A. P. Mitchell. 1999. Rapid hypothesis testing with *Candida albicans* through gene disruption with short homology regions. Journal of Bacteriology. 181(6):1868–74.

Zhu, J., W. Kempenaers, D. Van der Straeten, R. Contreras, and W. Fiers. 1985. A method for fast and pure DNA elution from agarose gels by centrifugal filtration. Bio/Technology. 3: 1014–1016.

TABLE 1

| Seq ID No. | Clone | Function |
|---|---|---|
| 1 | 382c_cp | — |
| 2 | 392c_cp | TUF1 |
| 3 | — | RAD53 |
| 4 | 417c_cpG2L | — |
| 5 | 325c_af | — |
| 6 | 322c_cp[1] | — |
| 7 | 26g3 | — |
| 8 | 409c_cp | — |
| 9 | 382c_cpG1L2 | — |
| 10 | 382c_cp (prt) | — |
| 11 | 392c_cp (prt) | TUF1 |
| 12 | | RAD53 |
| 13 | 325c_af (prt)[2] | — |
| 14 | 322c_cp (prt)[2] | — |
| 15 | 26g3 (prt) | — |
| 16 | 417c_cp 92L (prt) | — |

[1]322c-cp is a member of the UPF0057 protein family. It contains potential transmembrane regions (6-23aa; 30-53aa) and could be low temperature or salt-stress inducible.

[2]325c-af shows similarity to IMP4 yeast and related proteins and it might be involved in rRNA processing in *Candida albicans* in a similar way to IMP4.

The invention claimed is:

1. An isolated *Candida albicans* nucleic acid molecule selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 or SEQ ID NO: 9.

2. The isolated *Candida albicans* nucleic acid molecule of claim 1 which is SEQ ID NO: 1, SEQ ID NO: 2, or SEQ ID NO: 3.

3. The isolated *Candida albicans* nucleic acid molecule of claim 1 which is SEQ ID NO: 1, or SEQ ID NO: 2.

4. Isolated host cells containing an isolated *Candida albicans* DNA nucleic acid molecule consisting of SEQ ID NO: 1, SEQ NO: 2, SEQ ID NO: 3, SEQ ID NO: 4, SEQ ID NO: 5, SEQ ID NO: 6, SEQ ID NO: 7, SEQ ID NO: 8 or SEQ ID NO: 9, wherein said cells are bacterial or eukaryotic.

5. A recombinant DNA construct comprising an isolated *Candida albicans* nucleic acid molecule consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 or SEQ ID NO: 9, wherein the nucleic acid molecule is DNA.

* * * * *